United States Patent
Cruise et al.

(10) Patent No.: US 10,328,175 B2
(45) Date of Patent: Jun. 25, 2019

(54) POLYMER PARTICLES

(71) Applicant: MicroVention, Inc., Aliso Viejo, CA (US)

(72) Inventors: Gregory M. Cruise, Rancho Santa Margarita, CA (US); Xinping Wu, Aliso Viejo, CA (US); Gloria Hincapie, Aliso Viejo, CA (US); Yue Wu, Aliso Viejo, CA (US)

(73) Assignee: TERUMO CORPORATION, Tokyo (JP)

( * ) Notice: Subject to any disclaimer, the term of this patent is extended or adjusted under 35 U.S.C. 154(b) by 0 days.

(21) Appl. No.: 15/719,197

(22) Filed: Sep. 28, 2017

(65) Prior Publication Data
US 2018/0085487 A1    Mar. 29, 2018

Related U.S. Application Data

(60) Provisional application No. 62/428,990, filed on Dec. 1, 2016, provisional application No. 62/401,091, filed on Sep. 28, 2016.

(51) Int. Cl.
*A61L 24/00* (2006.01)
*A61K 47/69* (2017.01)
(Continued)

(52) U.S. Cl.
CPC ...... *A61L 24/0015* (2013.01); *A61K 31/4745* (2013.01); *A61K 31/555* (2013.01); *A61K 47/6927* (2017.08); *A61L 24/0042* (2013.01); *A61L 24/06* (2013.01); *A61L 26/009* (2013.01); *A61L 26/0014* (2013.01); *A61L 26/0061* (2013.01); *A61L 31/048* (2013.01); *A61L 31/148* (2013.01); *C08F 220/56* (2013.01); *C08F 236/20* (2013.01); *A61B 17/12109* (2013.01); *A61B 17/12113* (2013.01); *A61B 17/12181* (2013.01); *A61B 2017/00004* (2013.01); *A61L 2300/204* (2013.01);
(Continued)

(58) Field of Classification Search
CPC ............ A61L 24/0015; A61L 24/0042; A61L 26/009; A61L 31/148; A61K 47/6927
See application file for complete search history.

(56) References Cited

U.S. PATENT DOCUMENTS

| | | |
|---|---|---|
| 4,070,348 A | 1/1978 | Kraemer et al. |
| 4,157,323 A | 6/1979 | Yen et al. |

(Continued)

FOREIGN PATENT DOCUMENTS

| | | |
|---|---|---|
| CN | 103709323 A | 4/2014 |
| EP | 0240424 B1 | 5/1991 |

(Continued)

OTHER PUBLICATIONS

Blinova et al., Poly(ethylene glycol) containing functionalized polymer membranes for carbon dioxide separation. Preprints—American Chemical Society, Division of Energy & Fuels, 59(1):433-434 (2014).

(Continued)

*Primary Examiner* — Carlos A Azpuru
(74) *Attorney, Agent, or Firm* — K&L Gates LLP; Louis C. Cullman; Brian J. Novak

(57) ABSTRACT

Described are polymers and methods of forming and using same.

18 Claims, 2 Drawing Sheets

(51) Int. Cl.
  *A61K 31/4745* (2006.01)
  *A61K 31/555* (2006.01)
  *A61L 24/06* (2006.01)
  *C08F 220/56* (2006.01)
  *A61L 31/04* (2006.01)
  *A61L 31/14* (2006.01)
  *C08F 236/20* (2006.01)
  *A61L 26/00* (2006.01)
  *A61B 17/12* (2006.01)
  *A61B 17/00* (2006.01)

(52) U.S. Cl.
  CPC ..... *A61L 2300/224* (2013.01); *A61L 2400/06* (2013.01); *A61L 2430/36* (2013.01)

(56) References Cited

U.S. PATENT DOCUMENTS

| | | |
|---|---|---|
| 4,925,677 A | 5/1990 | Feijen |
| 5,417,982 A | 5/1995 | Modi |
| 5,545,423 A | 8/1996 | Soon-Shiong et al. |
| 5,635,215 A | 6/1997 | Boschetti et al. |
| 5,648,100 A | 7/1997 | Boschetti et al. |
| 5,662,935 A | 9/1997 | Motta |
| 5,759,578 A | 6/1998 | Soon-Shiong et al. |
| 5,879,709 A | 3/1999 | Soon-Shiong et al. |
| 5,906,997 A | 5/1999 | Schwartz et al. |
| 5,922,357 A | 7/1999 | Coombes et al. |
| 6,087,450 A | 7/2000 | Breitbach et al. |
| 6,218,440 B1 | 4/2001 | Kitagawa |
| 6,248,363 B1 | 6/2001 | Yoshikawa et al. |
| 6,306,922 B1 | 10/2001 | Hubbell et al. |
| 6,309,669 B1 | 10/2001 | Setterstrom et al. |
| 6,403,569 B1 | 6/2002 | Achterrath |
| 6,548,081 B2 | 4/2003 | Sadozai et al. |
| 6,555,138 B1 | 4/2003 | Karlsson et al. |
| 6,569,463 B2 | 5/2003 | Patel et al. |
| 6,689,374 B2 | 2/2004 | Chu et al. |
| 6,790,456 B2 | 9/2004 | Vogel et al. |
| 6,794,370 B2 | 9/2004 | Achterrath |
| 6,923,988 B2 | 8/2005 | Patel et al. |
| 6,946,146 B2 | 9/2005 | Muyle |
| 7,070,809 B2 | 7/2006 | Goupil et al. |
| 7,094,369 B2 | 8/2006 | Buiser et al. |
| 7,144,588 B2 | 12/2006 | Oray et al. |
| 7,153,572 B2 | 12/2006 | Cooper et al. |
| 7,442,385 B2 | 10/2008 | Lewis et al. |
| 7,449,236 B2 | 11/2008 | Lanphere et al. |
| 7,462,366 B2 | 12/2008 | Lanphere et al. |
| 7,588,780 B2 | 9/2009 | Buiser et al. |
| 7,591,993 B2 | 9/2009 | Boschetti |
| 7,670,592 B2 | 3/2010 | Boschetti |
| 7,736,671 B2 | 6/2010 | DiCarlo et al. |
| 7,776,240 B2 | 8/2010 | Chu et al. |
| 7,794,755 B2 | 9/2010 | Figuly et al. |
| 7,838,035 B2 | 11/2010 | Figuly |
| 7,838,699 B2 | 11/2010 | Schwarz et al. |
| 7,842,377 B2 | 11/2010 | Lanphere et al. |
| 7,858,119 B1 | 12/2010 | Odidi et al. |
| 7,887,846 B2 | 2/2011 | Figuly |
| 7,897,179 B2 | 3/2011 | Muyle |
| 7,951,402 B2 | 5/2011 | Lanphere et al. |
| 8,062,673 B2 | 11/2011 | Figuly et al. |
| 8,110,226 B2 | 2/2012 | Li |
| 8,143,042 B2 | 3/2012 | Bettinger et al. |
| 8,182,807 B2 | 5/2012 | Labhasetwar et al. |
| 8,201,689 B2 | 6/2012 | Kaem |
| 8,226,926 B2 | 7/2012 | Reb |
| 8,252,302 B2 | 8/2012 | Macdonald |
| 8,323,698 B2 | 12/2012 | Gu et al. |
| 8,323,794 B2 | 12/2012 | Chu et al. |
| 8,329,224 B2 | 12/2012 | Hall et al. |
| 8,367,099 B2 | 2/2013 | Herweck et al. |
| 8,383,758 B2 | 2/2013 | Papisov |
| 8,426,481 B2 | 4/2013 | Hassleholm et al. |
| 8,617,132 B2 | 12/2013 | Golzarian et al. |
| 8,673,266 B2 | 3/2014 | Boschetti |
| 8,691,791 B2 | 4/2014 | Lewis et al. |
| 8,697,137 B2 | 4/2014 | Vogel et al. |
| 8,709,384 B2 | 4/2014 | Reb |
| 8,739,978 B2 | 6/2014 | Yoon et al. |
| 8,741,351 B2 | 6/2014 | Vogel et al. |
| 9,938,367 B2 | 4/2018 | Cruise et al. |
| 2002/0028243 A1 | 3/2002 | Masters |
| 2002/0068089 A1 | 6/2002 | Vogel et al. |
| 2002/0071855 A1 | 6/2002 | Sadozai et al. |
| 2002/0197326 A1 | 12/2002 | Vogel et al. |
| 2003/0078339 A1 | 4/2003 | Kiser et al. |
| 2003/0183962 A1 | 10/2003 | Buiser et al. |
| 2003/0206864 A1 | 11/2003 | Mangin |
| 2004/0161466 A1 | 8/2004 | Lewis et al. |
| 2005/0196702 A1 | 9/2005 | Bryant et al. |
| 2005/0267556 A1 | 12/2005 | Shuros et al. |
| 2006/0025560 A1 | 2/2006 | Inoue et al. |
| 2006/0069168 A1 | 3/2006 | Tabata et al. |
| 2006/0222596 A1 | 10/2006 | Askari et al. |
| 2006/0240435 A1 | 10/2006 | Minoura et al. |
| 2006/0251582 A1 | 11/2006 | Reb |
| 2007/0035296 A1 | 2/2007 | Potapov et al. |
| 2007/0213683 A1 | 9/2007 | Cassingham et al. |
| 2007/0237741 A1 | 10/2007 | Figuly et al. |
| 2007/0237742 A1 | 10/2007 | Figuly et al. |
| 2007/0237830 A1 | 10/2007 | Figuly |
| 2007/0237956 A1 | 10/2007 | Figuly et al. |
| 2008/0033366 A1 | 2/2008 | Matson et al. |
| 2008/0039890 A1 | 2/2008 | Matson et al. |
| 2008/0102029 A1 | 5/2008 | Fritz et al. |
| 2008/0113029 A1 | 5/2008 | Fritz et al. |
| 2008/0220077 A1 | 9/2008 | Vogel et al. |
| 2009/0029077 A1 | 1/2009 | Atanasoska et al. |
| 2009/0092677 A1 | 4/2009 | Richard |
| 2009/0117033 A1 | 5/2009 | O'Gara |
| 2009/0164013 A1 | 6/2009 | Cruise et al. |
| 2009/0246275 A1 | 10/2009 | O'Gara et al. |
| 2009/0253809 A1 | 10/2009 | Gomurashvili et al. |
| 2010/0028260 A1 | 2/2010 | Fritz et al. |
| 2010/0040688 A1 | 2/2010 | Elbert et al. |
| 2010/0057027 A1 | 3/2010 | Furno et al. |
| 2010/0166876 A1 | 7/2010 | Lewis et al. |
| 2010/0247667 A1 | 9/2010 | Ariga et al. |
| 2010/0261646 A1 | 10/2010 | Lavik et al. |
| 2011/0009327 A1 | 1/2011 | Hill et al. |
| 2011/0009520 A1 | 1/2011 | Figuly et al. |
| 2011/0033548 A1 | 2/2011 | Lai et al. |
| 2011/0033608 A1 | 2/2011 | Figuly et al. |
| 2011/0038936 A1 | 2/2011 | Griswold et al. |
| 2011/0082427 A1 | 4/2011 | Golzarian et al. |
| 2011/0091550 A1 | 4/2011 | Zhang et al. |
| 2011/0152765 A1 | 6/2011 | Weber et al. |
| 2011/0182998 A1 | 7/2011 | Reb et al. |
| 2011/0212179 A1 | 9/2011 | Liu |
| 2012/0129798 A1 | 5/2012 | Akala et al. |
| 2012/0135170 A1 | 5/2012 | Meldal et al. |
| 2012/0213831 A1 | 8/2012 | Vogel et al. |
| 2012/0276151 A1 | 11/2012 | Lewis et al. |
| 2012/0289995 A1 | 11/2012 | Constant et al. |
| 2012/0302654 A1* | 11/2012 | Cruise .................. A61K 9/0024 521/149 |
| 2013/0052142 A1 | 2/2013 | Harder et al. |
| 2013/0190795 A1 | 7/2013 | Matson et al. |
| 2013/0315838 A1 | 11/2013 | Reb et al. |
| 2013/0323306 A1 | 12/2013 | Weber |
| 2014/0162969 A1 | 6/2014 | Lewis et al. |
| 2014/0186601 A1 | 7/2014 | Chang et al. |
| 2015/0079328 A1 | 3/2015 | Cruise et al. |
| 2015/0079395 A1* | 3/2015 | Cruise .................. C08F 220/56 428/402 |
| 2015/0166696 A1 | 6/2015 | Plotkin et al. |
| 2015/0306227 A1 | 10/2015 | Cruise et al. |
| 2016/0279282 A1 | 9/2016 | Cruise et al. |
| 2016/0311990 A1 | 10/2016 | Cruise et al. |

(56) References Cited

U.S. PATENT DOCUMENTS

| | | |
|---|---|---|
| 2017/0081450 A1 | 3/2017 | Cruise et al. |
| 2018/0085497 A1 | 3/2018 | Hincapie et al. |

FOREIGN PATENT DOCUMENTS

| | | |
|---|---|---|
| EP | 1534351 B1 | 10/2006 |
| EP | 1820495 A2 | 8/2007 |
| EP | 1267839 B1 | 10/2007 |
| EP | 2269580 A2 | 1/2011 |
| EP | 1796644 B1 | 4/2011 |
| EP | 1986706 B1 | 8/2011 |
| EP | 2368581 A2 | 9/2011 |
| EP | 2475695 B1 | 4/2014 |
| EP | 2286799 B1 | 7/2015 |
| JP | H05-279416 A | 10/1993 |
| JP | 2003-245544 A | 9/2003 |
| JP | 2011-201031 A | 10/2011 |
| JP | 2011-245267 A | 12/2011 |
| JP | 2012-170773 A | 9/2012 |
| JP | 2012-187308 A | 10/2012 |
| JP | 2014-218439 A | 11/2014 |
| WO | 1995/019186 A2 | 7/1995 |
| WO | 2001/072281 A2 | 10/2001 |
| WO | 2002/015913 A1 | 2/2002 |
| WO | 2002/071994 A1 | 9/2002 |
| WO | 2003/094930 A1 | 11/2003 |
| WO | 2006/081517 A2 | 8/2006 |
| WO | 2006/119968 A2 | 11/2006 |
| WO | 2007/035296 A2 | 3/2007 |
| WO | 2007/133020 A1 | 11/2007 |
| WO | 2008/034911 A1 | 3/2008 |
| WO | 2008/047095 A1 | 4/2008 |
| WO | 2008/057163 A2 | 5/2008 |
| WO | 2008/128580 A1 | 10/2008 |
| WO | 2008/136536 A1 | 11/2008 |
| WO | 2009/015281 A2 | 1/2009 |
| WO | 2009/040434 A1 | 4/2009 |
| WO | 2009/073193 A2 | 6/2009 |
| WO | 2009/131982 A1 | 10/2009 |
| WO | 2010/063630 A2 | 6/2010 |
| WO | 2011/014722 A2 | 2/2011 |
| WO | 2011/029867 A1 | 3/2011 |
| WO | 2011/068455 A1 | 6/2011 |
| WO | 2012/073188 A1 | 6/2012 |
| WO | 2012/120138 A1 | 9/2012 |
| WO | 2012/121073 A1 | 9/2012 |
| WO | 2012/133737 A1 | 10/2012 |
| WO | 2012/145431 A2 | 10/2012 |
| WO | 2012/166594 A1 | 12/2012 |
| WO | 2013/130143 A2 | 9/2013 |
| WO | 2013/177364 A1 | 11/2013 |
| WO | 2014/034787 A1 | 3/2014 |
| WO | 2015/042461 A1 | 3/2015 |
| WO | 2015/042462 A1 | 3/2015 |
| WO | 2015/070094 A1 | 5/2015 |
| WO | 2016/154592 A1 | 9/2016 |
| WO | 2018/064389 A1 | 4/2018 |
| WO | 2018/064390 A1 | 4/2018 |

OTHER PUBLICATIONS

International Search Report and Written Opinion dated Dec. 24, 2014 for International Application No. PCT/US2014/056647 filed on Sep. 19, 2014.

International Search Report and Written Opinion dated Feb. 27, 2015 for International Application No. PCT/US2014/064680 filed on Nov. 7, 2014.

International Search Report and Written Opinion dated Dec. 24, 2014 for International Application No. PCT/US2014/056644 filed on Sep. 19, 2014.

Kamitani et al., Design of cell-surface-retained polymers for artificial ligand display. ChemBioChem, 10(2):230-233 (2009).

Supplementary European Search Report dated Apr. 19, 2017 for European Application No. 14845609.

Supplementary European Search Report dated Apr. 6, 2017 for European Application No. 14845676.7.

International Search Report and Written Opinion dated Jun. 2, 2016 for International Application No. PCT/US2016/024340 filed on Mar. 25, 2016.

Tarasyuk et al., Investigation into the influence of organic modifiers and ultradispersed hybrid fillers on the structure and properties of glass-ceramic coatings prepared by the sol-gel method. Glass Physics and Chemistry, vol. 32, No. 4, pp. 439-447 (2006).

U.S. Appl. No. 15/604,529, filed May 24, 2017.

European Search Report and Search Opinion dated Jul. 10, 2017 for European Patent Application Serial No. 14859554.9.

International Search Report and Written Opinion dated Dec. 20, 2017 for International Application No. PCT/US2017/054118 filed on Sep. 28, 2017.

International Search Report and Written Opinion dated Feb. 27, 2018 for International Application No. PCT/US2017/054113 filed on Sep. 28, 2017.

U.S. Appl. No. 15/910,976, filed Mar. 2, 2018.

U.S. Appl. No. 15/878,294, filed Jan. 23, 2018.

\* cited by examiner

POLYMER PARTICLES

CROSS REFERENCE TO RELATED APPLICATIONS

This application claims the benefit of U.S. provisional patent application No. 62/401,091, filed Sep. 28, 2016 and U.S. provisional patent application No. 62/428,990, filed Dec. 1, 2016, the entire disclosures each of which is incorporated herein by reference.

FIELD

Described herein are polymeric particles configured for intravascular delivery of pharmaceutical agents, e.g., to a diseased site. Preparation of these polymer particles is also described.

SUMMARY

Described herein are polymer particles. In some embodiments, the particles are hydrogel particles. These particles can be configured to deliver pharmaceutical agents and can also be used for embolization. In some embodiments, the polymers used herein can include at least one monomer amenable to polymerization, at least one crosslinker, and at least one pharmaceutical agent chemically bonded to the particle with a hydrolytically degradable linkage. In some embodiments, the pharmaceutical agent can be a polymerizable pharmaceutical agent. As the hydrolytic linkage is broken, the pharmaceutical agent can be controllably released from the polymer particle.

In some embodiments, the polymer particle can be biostable. In some embodiments, the hydrogel particle can be biostable. In other embodiments, the crosslinker can be biostable. In other embodiments, the particle can be biodegradable and/or the crosslinker can be biodegradable.

In one embodiment, the polymerizable pharmaceutical agent can have a structure

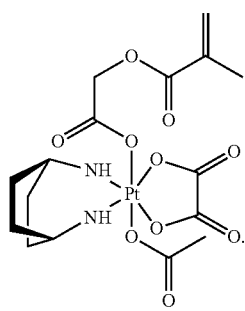

PPA 1

In another embodiment, the polymerizable pharmaceutical agent can have a structure

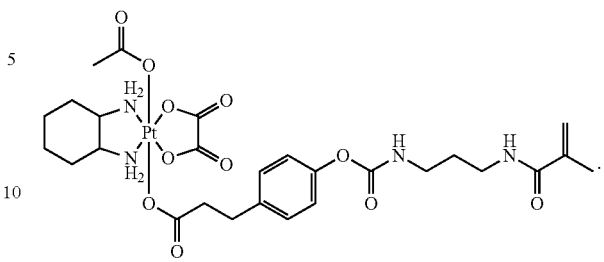

PPA 2

In another embodiment, the polymerizable pharmaceutical agent can have a structure

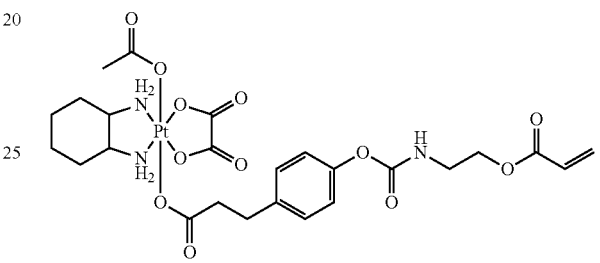

PPA 3

In another embodiment, the polymerizable pharmaceutical agent can have a structure

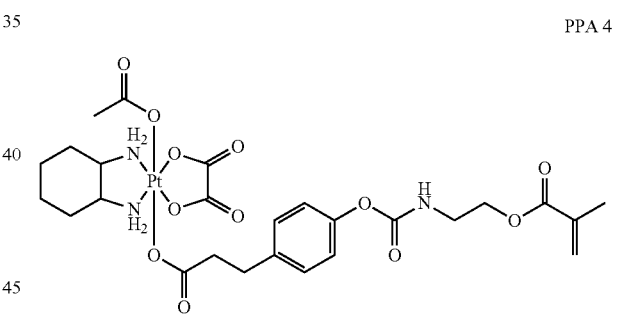

PPA 4

In another embodiment, the polymerizable pharmaceutical agent can have a structure

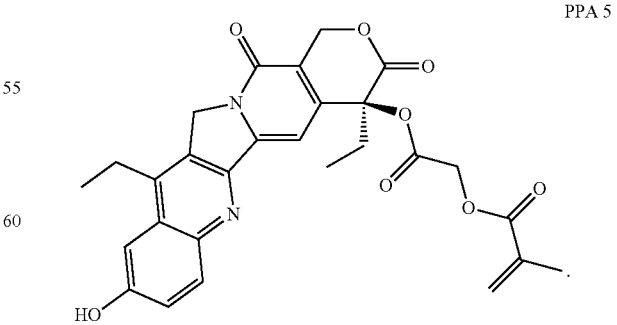

PPA 5

In another embodiment, the polymerizable pharmaceutical agent can have a structure

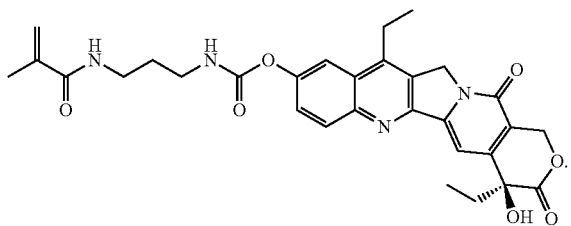

In another embodiment, the polymerizable pharmaceutical agent can have a structure

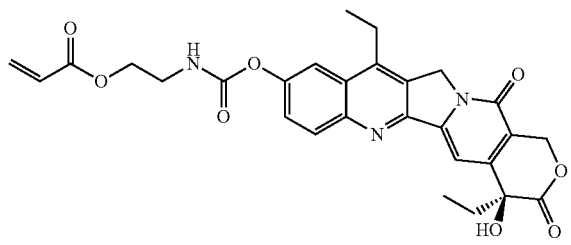

In another embodiment, the polymerizable pharmaceutical agent can have a structure

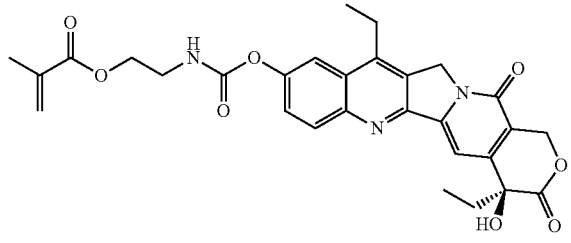

Methods are also described for forming polymer particles described herein. In some embodiments, methods can include reacting a prepolymer solution including the components included in the particle, such as but not limited to, at least one monomer amenable to polymerization, at least one crosslinker, and at least one pharmaceutical agent.

Also, described herein are methods for treating a vessel. The methods can include administering to the vessel a plurality of polymer particles as described herein. In other embodiments, the methods can include administering to the vessel a plurality of hydrogel particles as described herein.

DETAILED DESCRIPTION

Figure 1:
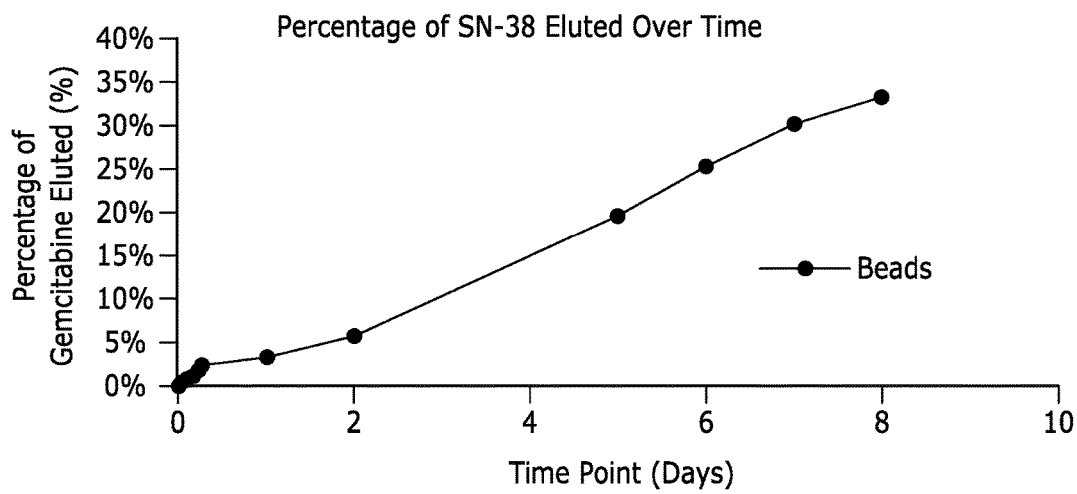
FIG. 1 illustrates the kinetics of SN-38 elution from the preloaded particles.

Described herein are polymeric or polymer particles. In some embodiments, the polymers are hydrogel particles. These particles can include a pharmaceutical agent that can be degradably attached to the particle. In some embodiments, this degradability can be through a hydrolytic, oxidative, or reductive linkage.

In some embodiments, the particles can comprise (i) at least one monomer amenable to polymerization, (ii) at least one crosslinker, and (iii) at least one polymerizable pharmaceutical agent.

In some embodiments, the monomer(s) and crosslinker(s) provide the physical properties of the particles. Desired physical properties can include elasticity and/or robustness to permit delivery through a microcatheter or catheter. The polymerizable pharmaceutical agent(s) can permit the controlled release of the pharmaceutical agent(s) from the particle.

Monomers generally are low molecular weight chemicals containing a single polymerizable group. The main functions of the monomers, if present, are to aid the polymerization of the hydrogel and to impart specific mechanical properties to the resulting hydrogel. The monomers can be any molecule with a single functionality to incorporate into the resulting hydrogel. In some embodiments, the monomers can include a structure conducive to a desired mechanical property.

Monomers can include acrylamide and/or acrylate monomers. Acrylamide monomers can include alkylacrylamide monomers. Acrylate monomers can include alkylacrylate monomers. Alkyl may be linear alkyl, branched alkyl, cycloalkyl, or a combination thereof, and in some embodiments, may contain from one to thirty-five carbon atoms. In some embodiments, the alkyl group can include a substituent such as a hydroxyl or glycerol group. Other types of acrylamide and acrylate monomers are also possible. In some embodiments, monomers can include acrylamide, methacrylamide, dimethyl acrylamide, glycerol monomethacrylate, hydroxypropyl acrylate, methyl methacrylate, combinations thereof, and derivatives thereof.

Monomer concentrations can range from about 5% w/w to about 50% w/w, about 10% w/w to about 50% w/w, about 5% w/w to about 40% w/w, about 10% w/w to about 50% w/w, about 20% w/w to about 50% w/w, about 20% w/w to about 40% w/w, or about 20% w/w to about 30% w/w of a prepolymer solution used to form the polymer.

In other embodiments, monomer concentrations can range from about 5% w/w to about 50% w/w, about 10% w/w to about 50% w/w, about 5% w/w to about 40% w/w, about 10% w/w to about 50% w/w, about 20% w/w to about 50% w/w, about 20% w/w to about 40% w/w, or about 20% w/w to about 30% w/w of a dried particle.

Crosslinkers, low molecular weight molecules with a plurality of polymerizable moieties, can also be optionally included to impart further cross-linking of the resulting particle. The crosslinker can be any molecule with at least two functionalities to incorporate into the resulting hydrogel. The crosslinkers can include a structure conducive to a desired mechanical property of the particle. Crosslinkers can include N,N'-methylenebisacrylamide, ethylene glycol dimethacrylate, or combinations thereof.

Further or alternatively, biodegradable crosslinkers can be utilized to allow for the particles to dissolve in vivo. Biodegradable crosslinkers can include esters, carbonates, oxalates, carbamates, thioesters, and combinations thereof. Crosslinker concentrations can be less than 50% of the moles of the prepolymer solution used to form the particles.

In some embodiments, a crosslinker can have a structure

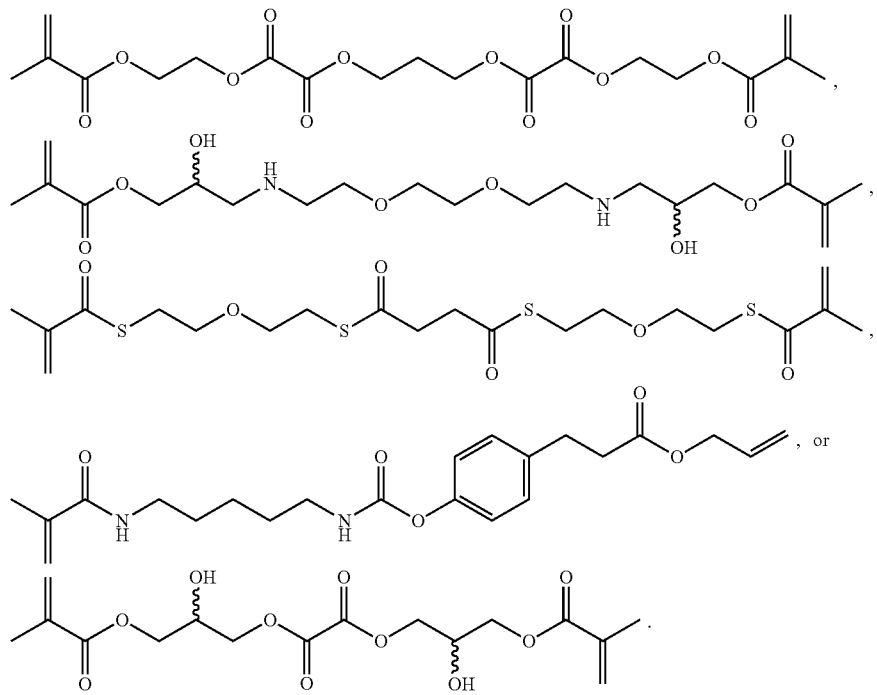

A polymerizable pharmaceutical agent can include a desired pharmaceutical agent chemically modified to permit incorporation into a particle polymer network and to permit decoupling from the particle in a controlled rate at a diseased site. The incorporation can be achieved by adding a moiety amenable to the polymerization mechanism selected for the particle. The modification can turn the pharmaceutical agent into a monomer. The decoupling can be achieved by adding a linkage unstable in a physiological environment between the polymerization group and the pharmaceutical agent. This linkage can break via hydrolytic, oxidative, or reductive mechanisms available in the physiological environment.

A polymerizable pharmaceutical agent can be a polymerizable variant of an anticancer drug, an anti-inflammatory drug, an anti-thrombotic drug, an anti-proliferative drug, a derivative thereof, or the like.

In one embodiment, the polymerizable pharmaceutical agent can be an anticancer drug.

In one embodiment, the polymerizable pharmaceutical agent can be a polymerizable derivative of oxaliplatin.

In another embodiment, the polymerizable pharmaceutical agent can be an oxaliplatin polymerizable derivative having a structure In another embodiment, the polymerizable pharmaceutical agent can be an oxaliplatin polymerizable derivative having a structure

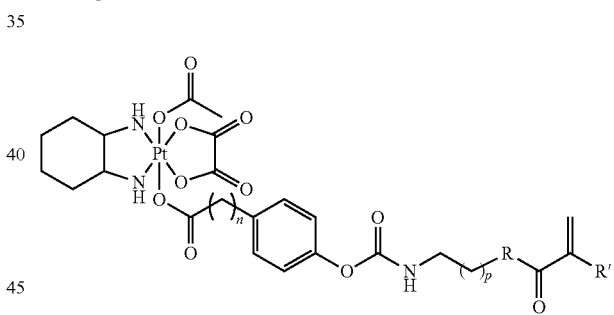

wherein n is 0, 1, 2, 3, 4, 5, 6, 7, 8, 9, 10, 11, or 12; p is 1, 2, 3, 4, 5, 6, 7, 8, 9, 10, 11, or 12; R is O or NH; and R' is H or $CH_3$.

In one embodiment, the polymerizable pharmaceutical agent can be an oxaliplatin polymerizable derivative having a structure

PPA 1

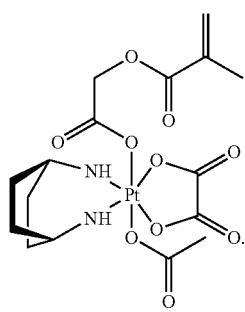

PPA 2

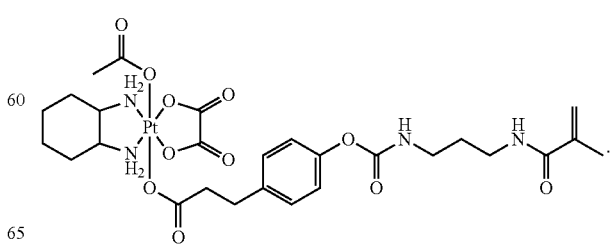

In another embodiment, the polymerizable pharmaceutical agent can be an oxaliplatin polymerizable derivative having a structure

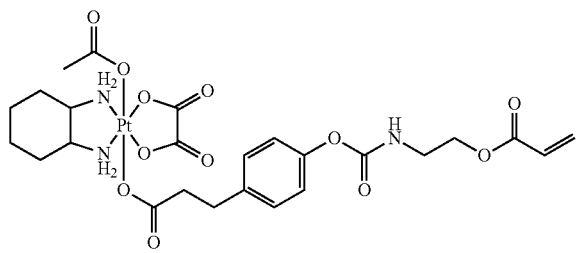

PPA 3

In another embodiment, the polymerizable pharmaceutical agent can be an oxaliplatin polymerizable derivative having a structure

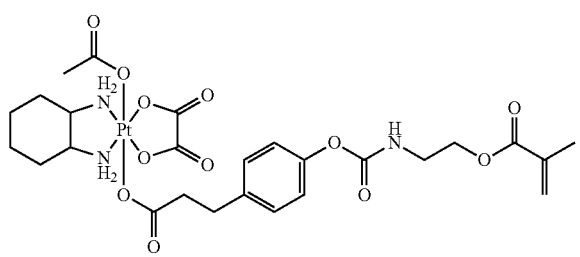

PPA 4

In another embodiment, the polymerizable pharmaceutical agent can be a polymerizable derivative of SN-38 (7-ethyl-10-hydroxy-camptothecin).

In another embodiment, the polymerizable pharmaceutical agent can be a SN-38 polymerizable derivative having a structure

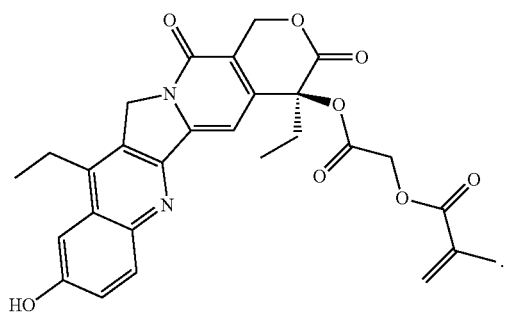

PPA 5

In some embodiments, the polymerizable pharmaceutical agent can be (S)-2-((4,11-diethyl-9-hydroxy-3,14-dioxo-3,4,12,14-tetrahydro-1H-pyrano[3',4':6,7]indolizino[1,2-b]quinolin-4-yl)oxy)-2-oxoethyl methacrylate.

In another embodiment, the polymerizable pharmaceutical agent can be a SN-38 polymerizable derivative having a structure

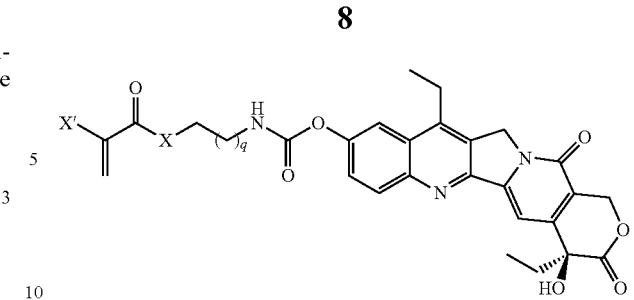

wherein q is 1, 2, 3, 4, 5, 6, 7, 8, 9, 10, 11, or 12; X is O or NH; and X' is H or CH$_3$.

In one embodiment, the polymerizable pharmaceutical agent can be a SN-38 polymerizable derivative having a structure

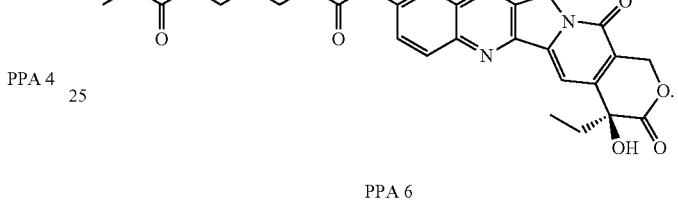

PPA 6

In another embodiment, the polymerizable pharmaceutical agent can be a SN-38 polymerizable derivative having a structure

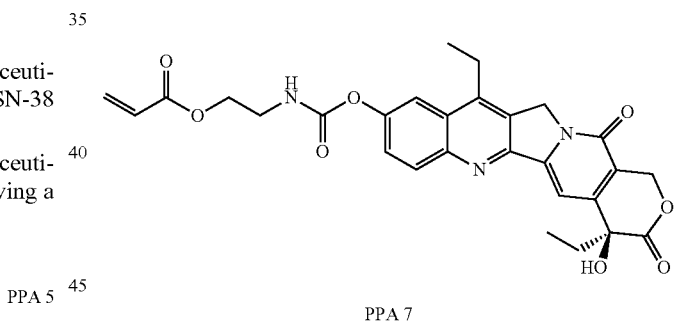

PPA 7

In another embodiment, the polymerizable pharmaceutical agent can be a SN-38 polymerizable derivative having a structure

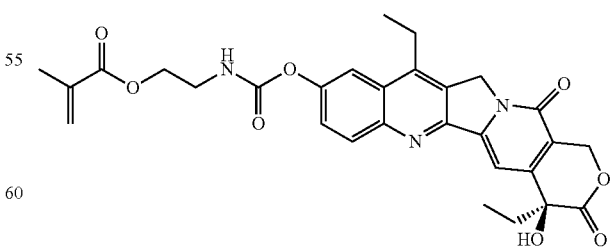

PPA 8

In some embodiments, the polymerizable pharmaceutical agent can be (S)-2-((((4,11-diethyl-4-hydroxy-3,14-dioxo-3, 4,12,14-tetrahydro-1H-pyrano[3',4':6,7]indolizino[1,2-b]quinolin-9-yl)oxy)carbonyl)amino)ethyl methacrylate.

Linkages susceptible to breakage in a physiological environment include those susceptible to hydrolysis, including esters, thioesters, carbamates, oxalates, and carbonates, and those susceptible to enzymatic action, including peptides that are cleaved by matrix metalloproteinases, collagenases, elastases, and cathepsins. Multiple decoupling linkages can be utilized to control the rate of release of the pharmaceutical agent in a manner that is not possible with only one, i.e. one linkage to permit a large, rapid release immediately following implantation and another linkage to permit a slow, sustained release over longer periods of time.

After particle preparation with incorporated pharmaceutical agents, extensive washing of the particles can be performed without prematurely releasing the pharmaceutical agent. Once the particle is delivered to the diseased site, the pharmaceutical agent can decouple from the particle as the linkage breaks.

In some embodiments, to permit polymerization of the monomers/crosslinkers/polymerizable pharmaceutical agent, all the components of the particle have moieties conducive to a polymerization reaction. In some embodiments, a polymerization mechanism used is free radical polymerization. If free radical polymerization is utilized to prepare the particles, all components can have ethylenically unsaturated moieties. Functionalities for free radical polymerization include acrylates, methacrylates, vinyl groups, and derivatives thereof. Alternatively, other reactive chemistries can be employed to polymerize the hydrogel, i.e. nucleophile/N-hydroxysuccinimide esters, vinyl sulfone/acrylate, thiol-ene, or maleimide/acrylate. In some embodiments, functional groups of the monomers/crosslinkers/polymerizable pharmaceutical agents can be acrylates and methacrylates.

In other embodiments, if desired, the particle can be designed to dissolve in vivo, or biodegrade. Linkages unstable in the physiological environment can be introduced to the macromer or crosslinker to impart biodegradation by hydrolytic, oxidative, or reductive mechanisms. Linkages susceptible to breakage in a physiological environment include those susceptible to hydrolysis, including esters, thioesters, carbamates, oxalates, and carbonates, and those susceptible to enzymatic action, including peptides that are cleaved by matrix metalloproteinases, collagenases, elastases, and cathepsins. Multiple crosslinkers can be utilized to control the rate of degradation in a manner that is not possible with only one.

Visualization of particles may be desired using medically relevant imaging techniques such as fluoroscopy, computed tomography, or magnetic resonant imaging to permit intravascular delivery and follow-up. Visualization of the particles under fluoroscopy can be imparted by the incorporation of solid particles of radiopaque materials such as barium, bismuth, tantalum, platinum, gold, and other dense metals into the particles or by the incorporation of iodine-containing molecules polymerized into the particle structure.

Visualization agents for fluoroscopy can include barium sulfate and iodine-containing molecules. Visualization of the particles under computed tomography imaging can be imparted by incorporation of solid particles of barium or bismuth or by the incorporation of iodine-containing molecules polymerized into the particle structure.

Metals visible under fluoroscopy generally result in beam hardening artifacts that preclude the usefulness of computed tomography imaging for medical purposes. Visualization agents for computed tomography are barium sulfate and iodine-containing molecules. Barium sulfate concentrations that can render the particles visible using fluoroscopic and computed tomography imaging range from about 30% w/w to about 60% w/w, about 30% w/w to about 50% w/w, about 30% w/w to about 40% w/w, about 40% w/w to about 50% w/w, about 40% w/w to about 60% w/w, or about 45% w/w to about 60% w/w of the prepolymer solution used to form the particles.

Iodine concentrations that can render the particles visible using fluoroscopy and/or computed tomography range from about 80 mg to about 500 mg of the prepolymer solution used to form the particles.

Visualization of the particles under magnetic resonance imaging can be imparted by the incorporation of solid particles of superparamagnetic iron oxide or gadolinium molecules polymerized into the particle structure. A visualization agent for magnetic resonance is superparamagnetic iron oxide with a particle size of about 10 microns. Concentrations of superparamagnetic iron oxide particles to render the particles visible using magnetic resonance imaging range from about 0.1% to about 1% w/w of the prepolymer solution used to form the particles.

Methods of forming polymer particles can include reacting a prepolymer solution including the components included in the polymer particle, such as but not limited to at least one monomer amenable to polymerization, at least one crosslinker, and at least one pharmaceutical agent.

Methods of forming hydrogel particles can include reacting a prepolymer solution including the components included in the polymer particle, such as but not limited to at least one monomer amenable to polymerization, at least one crosslinker; and at least one pharmaceutical agent.

The prepolymer solution including the polymerizable components can be polymerized by reduction-oxidation, radiation, heat, or any other method known in the art. Radiation cross-linking of the prepolymer solution can be achieved with ultraviolet light or visible light with suitable initiators or ionizing radiation (e.g. electron beam or gamma ray) without initiators. Cross-linking can be achieved by application of heat, either by conventionally heating the solution using a heat source such as a heating well, or by application of infrared light to the monomer solution. The free radical polymerization of the monomer(s) and crosslinker(s) can be used and can utilize an initiator to start the reaction. In one embodiment, the cross-linking method utilizes azobisisobutyronitrile (AIBN) or another water soluble AIBN derivative (2,2'-azobis(2-methylpropionamidine) dihydrochloride). Other cross-linking agents useful according to the present description include N,N,N',N'-tetramethylethylenediamine, ammonium persulfate, benzoyl peroxides, and combinations thereof, including azobisisobutyronitriles. In one embodiment, the initiator is AIBN at a concentration range of about 2% to about 5% w/w of the prepolymer solution.

The prepolymer solution can be prepared by dissolving the monomer(s), crosslinker(s), and initiator(s) in a solvent. The particles can be prepared by emulsion polymerization. A non-solvent for the prepolymer solution, typically mineral oil when the monomer solvent is hydrophilic, and a surfactant are added to the reaction vessel. An overhead stirrer is placed in the reaction vessel. The reaction vessel is then sealed, and sparged with argon to remove any entrapped oxygen. The initiator component is added to the reaction vessel and stirring commenced. Additional initiator is added to the polymerization solution and both are then added to the reaction vessel, where the stirring suspends droplets of the prepolymer solution in the mineral oil.

The rate of stirring can affect particle size, with faster stirring producing smaller particles. Stirring rates can be about 100 rpm, about 200 rpm, about 300 rpm, about 400 rpm, about 500 rpm, about 600 rpm, about 700 rpm, about 800 rpm, about 900 rpm, about 1,000 rpm, about 1,100 rpm, about 1,200 rpm, about 1,300 rpm, between about 200 rpm and about 1,200 rpm, between about 400 rpm and about 1,000 rpm, at least about 100 rpm, at least about 200 rpm, at most about 1,300 rpm, or at most about 1,200 rpm to produce particles with desired diameters.

The particles can have diameters of about 10 µm, about 20 µm, about 30 µm, about 40 µm, about 50 µm, about 60 µm, about 75 µm, about 100 µm, about 200 µm, about 300 µm, about 400 µm, about 500 µm, about 600 µm, about 700 µm, about 800 µm, about 900 µm, about 1,000 µm, about 1,100 µm, about 1,200 µm, about 1,300 µm, about 1,400 µm, about 1,500 µm, about 1,600 µm, between about 50 µm and about 1,500 µm, between about 100 µm and about 1,000 µm, between about 75 µm and about 1,200 µm, at least about 50 µm, at least about 80 µm, at most about 1,500 µm, or at most about 1,200 µm. In some embodiments, the diameter can be between about 40 µm and about 1,200 µm, between about 40 µm and about 60 µm, or between about 75 µm and about 1,200 µm. In some embodiments, the particles can be referred to as microspheres or microparticles.

In some embodiments, the particles described herein can have a generally or substantially spherical shape.

In some embodiments, the polymer particles can retain their diameters even after injection through a catheter or other delivery device. In other words, the polymer particles may not fall apart or otherwise fracture during delivery. In some embodiments, the polymer particles can retain about 99%, about 98%, about 97%, about 96%, about 95%, about 90%, greater than about 99%, greater than about 98%, greater than about 97%, greater than about 96%, greater than about 95%, greater than about 90%, or between about 90% and about 100% of their diameter after delivery.

The particles can also have a characteristic circularity or have a relative shape that is substantially circular. This characteristic describes or defines the form of a region on the basis of its circularity. Particles as described herein can have a fraction of circularity of about 0.8, 0.9, 0.95, 0.96, 0.97, 0.98, 0.99, greater than about 0.8, greater than about 0.9, or greater than about 0.95. In one embodiment, the circularity of the particles is greater than about 0.9.

The particles can retain their circularity even after injection through a catheter or other delivery device. In some embodiments, the particles can retain about 99%, about 98%, about 97%, about 96%, about 95%, about 90%, greater than about 99%, greater than about 98%, greater than about 97%, greater than about 96%, greater than about 95%, greater than about 90%, or between about 90% and about 100% of their circularity after delivery.

Polymerization can be allowed to proceed as long as necessary to produce particles with desired resiliency. Polymerization can be allowed to proceed for about 1 hr, about 2 hr, about 3 hr, about 4 hr, about 5 hr, about 6 hr, about 7 hr, about 8 hr, about 9 hr, about 10 hr, about 11 hr, about 12 hr, about 18 hr, about 24 hr, about 48 hr, about 72 hr, about 96 hr, between about 1 hr and about 12 hr, between about 1 hr and about 6 hr, between about 4 hr and about 12 hr, between about 6 hr and about 24 hr, between about 1 hr and about 96 hr, between about 12 hr and about 72 hr, or at least about 6 hours.

Polymerization can be run at a temperature to produce particles with desired resiliency and/or reaction time. Polymerization can be run at a temperature of about 10° C., about 20° C., about 30° C., about 40° C., about 50° C., about 60° C., about 70° C., about 80° C., about 90° C., about 100° C., between about 10° C. and about 100° C., between about 10° C. and about 30° C., at least about 20° C., at most about 100° C., or at about room temperature. In one embodiment, polymerization occurs at room temperature.

In one embodiment, polymerization occurs overnight at room temperature.

After polymerization is complete, the particles can be washed to remove any solute, mineral oil, unreacted monomer(s), and unbound oligomers. Any solvent may be utilized, but care should be taken if aqueous solutions are used to wash particles with linkages susceptible to hydrolysis. In some embodiments, washing solutions can include hexanes, dimethylformamide, acetone, alcohols, water with surfactant, water, saline, buffered saline, and saline and a surfactant.

Optionally, the washed particles can then be dyed to permit visualization before injection into a microcatheter during preparation by the physician. A dye bath is made by dissolving sodium carbonate and the desired dye in water. Any of the dyes from the family of reactive dyes which bond covalently to the particle can be used. Dyes can include reactive blue 21, reactive orange 78, reactive yellow 15, reactive blue No. 19 reactive blue No. 4, C.I. reactive red 11, C.I. reactive yellow 86, C.I. reactive blue 163, C.I. reactive red 180, C.I. reactive black 5, C.I. reactive orange 78, C.I. reactive yellow 15, C.I. reactive blue No. 19, C.I. reactive blue 21, any of the color additives approved for use by the FDA part 73, subpart D, or any dye that will irreversibly bond to the particles. Particles can be added to the dye bath and stirred.

If the herein described particle does not adequately bind any of the reactive dyes described above, a monomer containing an amine can be added to the monomer solution in an amount to achieve the desired coloration. Even if the particle does adequately bind the reactive dyes described above, a monomer containing an amine can be added to the monomer solution. Examples of suitable amine containing monomers include aminopropyl methacrylate, aminoethyl methacrylate, aminopropyl acrylate, aminoethyl acrylate, derivatives thereof, combinations thereof, and salts thereof. In some embodiments, concentrations of the amine containing monomers in the final product can be less than or equal to about 1% w/w.

After the dying process, any unbound dye is removed through copious washing. After dying and additional washing, the particles can be packaged into vials or syringes, and sterilized.

The particles described herein can be sterilized without substantially degrading the polymer. After sterilization, at least about 50%, about 60%, about 70%, about 80%, about 90%, about 95% about 99% or about 100% of the polymer can remain intact. In one embodiment, the sterilization method can be autoclaving and can be utilized before administration.

The particles can be used to treat a mammal in need. Mammals can include, but are not limited to, humans, horses, camels, dogs, cats, cows, bears, rodents, oxen, bison, buffalo, caribou, moose, deer, elk, sheep, goats, pigs, rabbits, pouched mammals, primates, carnivores, or the like.

The polymers can be used to fill aneurysms, provide an embolus, fill vessel malformations, fill biological voids, provide pharmaceutical agents at a particular site, provide treatment to a surgical or injury site, or the like. The methods can include administering to the vessel a plurality of particles as described herein. In some embodiments, hydrogel particles can be formed that swell once delivered or once subjected to an appropriate condition.

The final particle preparation can be delivered to the site to be embolized via a catheter, microcatheter, needle, or similar delivery device. In some embodiments, a radiopaque contrast agent can be thoroughly mixed with the particles in a syringe and injected through a catheter or similar delivery device until blood flow is determined to be occluded from the site by interventional imaging techniques.

The particles can be delivered to a diseased site, with or without complete cessation of blood flow. Upon delivery to the diseased site, pharmaceutical agents can be released from the particles.

In some embodiments, the particles can be configured for embolization of hypervascularized tumors or arteriovenous malformations. In some embodiments, a patient can be selected that exhibits a hypervascularized tumor and/or an arteriovenous malformation. A microcatheter can be navigated to the location of the tumor or malformation. Particles as described herein can be injected into that site to stabilize it thereby treating the patient's condition.

In other embodiments, the particles can be injected through a needle to a treatment site(s).

In some embodiments, it may be desirable for the particles to degrade over time. In other words, the particles can be degradable and/or biodegradable. In such embodiments, the particles can degrade to less than about 40%, about 30% about 20%, about 10%, about 5%, or about 1% of their initial size after about 2 days, 3 days, 5 days, about 2 weeks, about 1 month, about 2 months, about 6 months, about 9 months, about a year, about 2 years, about 5 years, or about 10 years. In one embodiment, the particles can be substantially degraded in less than about 1 month. In another embodiment, the particles can be substantially degraded in less than about 6 months.

In some embodiments, degradability can be accelerated with an appropriate and/or adequate enzyme. In some embodiments, the particles can be injected along with an enzyme that can accelerate the degradation of the particles. In other embodiments, an enzyme can be delivered to the site of the implanted particles at a remote time and accelerate degradation at that time.

In some embodiments, the greater the percentage of a crosslinker in the final particles, the longer degradation takes. Additionally, the larger the particle diameter, the longer the degradation. Thus, the particles with the longest degradation time are those that have the largest concentration of crosslinker and the largest diameter. These two properties can be varied to tailor degradation time as needed.

The particles described herein can be compressible yet durable enough not to break apart or fragment. Substantially no change in circularity or diameter of particles occurs during delivery through a microcatheter. In other words, after delivery through a microcatheter, the polymer particles described herein remain greater than about 60%, about 70% about 80%, about 90%, about 95%, about 99% or about 100% intact after delivery.

Further, in some embodiments, the particles can stick to the tissue and/or remain in place through friction with the tissues. In other embodiments, the particles can act as a plug in a vessel held in place by the flow and pressure of the blood itself. In still other embodiments, the particles can be cohesive enough to stick to one another to aid in agglomerating particles at a particular site of action.

In some embodiments, the particles can include dimethyl acrylamide, glycerol monomethacrylate, and a polymerizable anticancer drug or a derivative thereof, crosslinked with

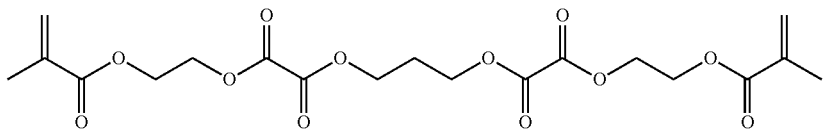

In some embodiments, the particles can include dimethyl acrylamide, glycerol monomethacrylate, and a polymerizable anticancer drug or a derivative thereof, crosslinked with

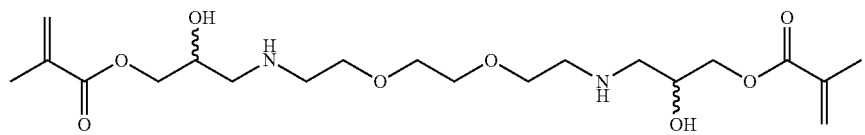

In some embodiments, the particles can include dimethyl acrylamide, glycerol monomethacrylate, and a polymerizable anticancer drug or a derivative thereof, crosslinked with

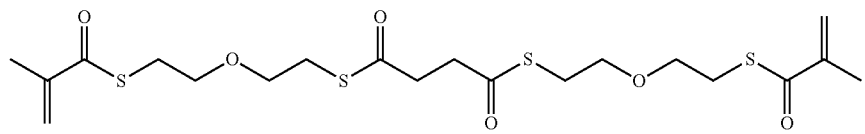

In some embodiments, the particles can include dimethyl acrylamide, glycerol monomethacrylate, and a polymerizable anticancer drug or a derivative thereof, crosslinked with

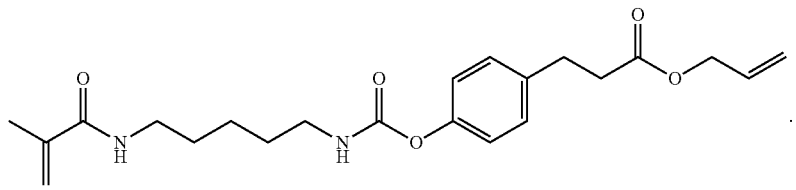 [SMILES: C=CCOC(=O)CCc1ccc(OC(=O)NCCCCCNC(=O)C(=C)C)cc1]

In some embodiments, the particles can include dimethyl acrylamide, glycerol monomethacrylate, and a polymerizable anticancer drug or a derivative thereof, crosslinked with

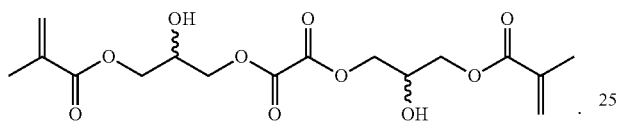

In some embodiments, the particles can include dimethyl acrylamide, glycerol monomethacrylate, and PPA1 or a derivative thereof, crosslinked with

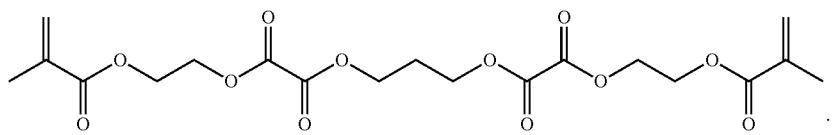 [SMILES: C=C(C)C(=O)OCCOC(=O)C(=O)OCCCOC(=O)C(=O)OCCOC(=O)C(=C)C]

In some embodiments, the particles can include dimethyl acrylamide, glycerol monomethacrylate, and PPA1 or a derivative thereof, crosslinked with

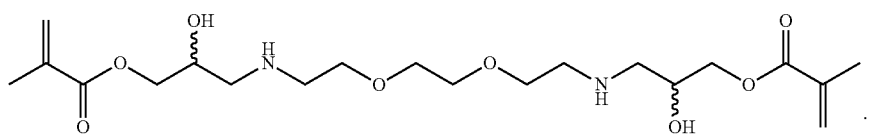 [SMILES: C=C(C)C(=O)OCC(O)CNCCOCCOCCNCC(O)COC(=O)C(=C)C]

In some embodiments, the particles can include dimethyl acrylamide, glycerol monomethacrylate, and PPA1 or a derivative thereof, crosslinked with

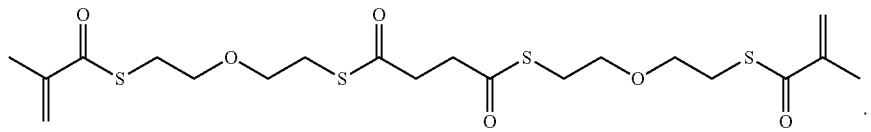 [SMILES: C=C(C)C(=O)SCCOCCSC(=O)CCC(=O)SCCOCCSC(=O)C(=C)C]

In some embodiments, the particles can include dimethyl acrylamide, glycerol monomethacrylate, and PPA1 or a derivative thereof, crosslinked with

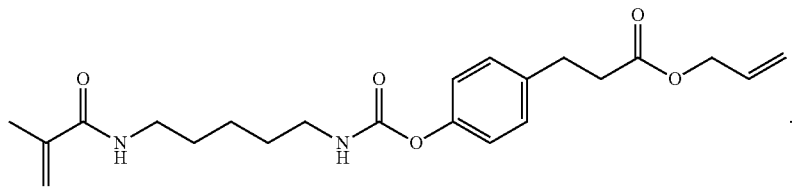 [SMILES: C=CCOC(=O)CCc1ccc(OC(=O)NCCCCCNC(=O)C(=C)C)cc1]

In some embodiments, the particles can include dimethyl acrylamide, glycerol monomethacrylate, and PPA1 or a derivative thereof, crosslinked with

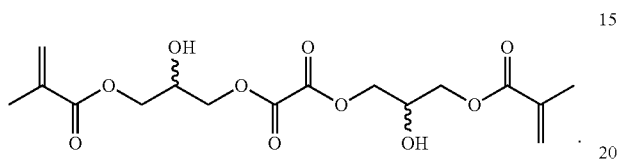

In some embodiments, the particles can include dimethyl acrylamide, glycerol monomethacrylate, and PPA2 or a derivative thereof, crosslinked with

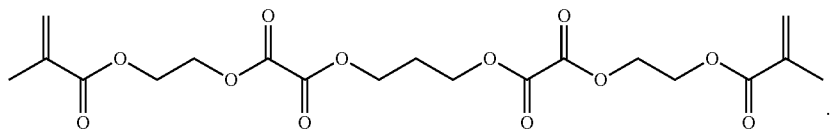 [SMILES: C=C(C)C(=O)OCCOC(=O)C(=O)OCCCOC(=O)C(=O)OCCOC(=O)C(=C)C]

In some embodiments, the particles can include dimethyl acrylamide, glycerol monomethacrylate, and PPA2 or a derivative thereof, crosslinked with

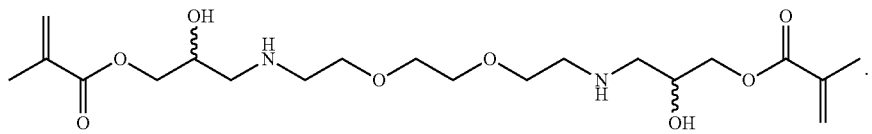 [SMILES: C=C(C)C(=O)OCC(O)CNCCOCCOCCNCC(O)COC(=O)C(=C)C]

In some embodiments, the particles can include dimethyl acrylamide, glycerol monomethacrylate, and PPA2 or a derivative thereof, crosslinked with

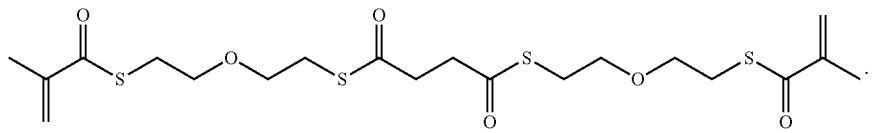 [SMILES: C=C(C)C(=O)SCCOCCSC(=O)CCC(=O)SCCOCCSC(=O)C(=C)C]

In some embodiments, the particles can include dimethyl acrylamide, glycerol monomethacrylate, and PPA2 or a derivative thereof, crosslinked with

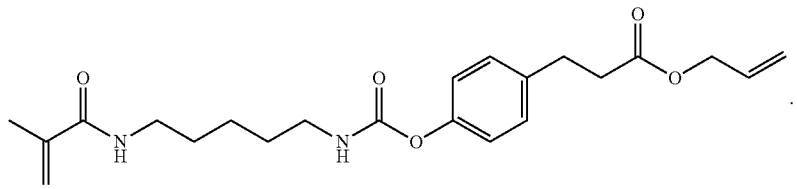 [SMILES: C=CCOC(=O)CCc1ccc(OC(=O)NCCCCCNC(=O)C(=C)C)cc1]

In some embodiments, the particles can include dimethyl acrylamide, glycerol monomethacrylate, and PPA2 or a derivative thereof, crosslinked with

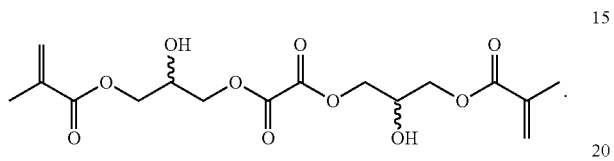

In some embodiments, the particles can include dimethyl acrylamide, glycerol monomethacrylate, and PPA3 or a derivative thereof, crosslinked with

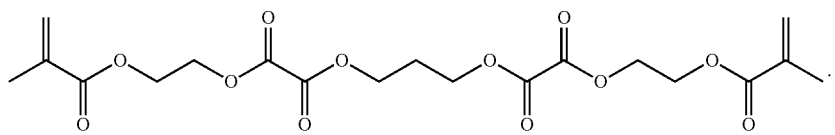 [SMILES: C=C(C)C(=O)OCCOC(=O)C(=O)OCCCOC(=O)C(=O)OCCOC(=O)C(=C)C]

In some embodiments, the particles can include dimethyl acrylamide, glycerol monomethacrylate, and PPA3 or a derivative thereof, crosslinked with

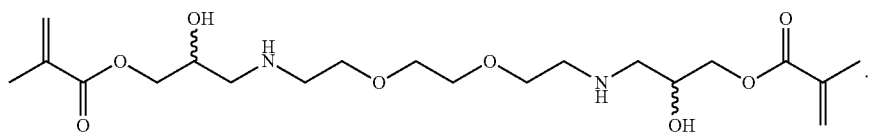 [SMILES: C=C(C)C(=O)OCC(O)CNCCOCCOCCNCC(O)COC(=O)C(=C)C]

In some embodiments, the particles can include dimethyl acrylamide, glycerol monomethacrylate, and PPA3 or a derivative thereof, crosslinked with

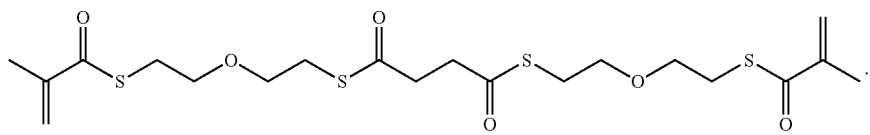 [SMILES: C=C(C)C(=O)SCCOCCSC(=O)CCC(=O)SCCOCCSC(=O)C(=C)C]

In some embodiments, the particles can include dimethyl acrylamide, glycerol monomethacrylate, and PPA3 or a derivative thereof, crosslinked with

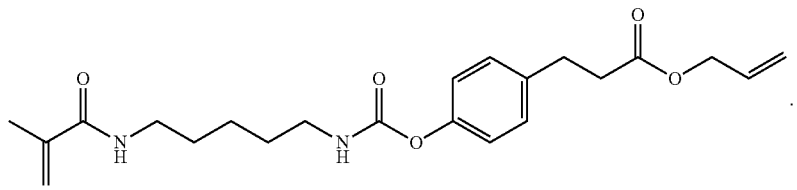 [SMILES: C=CCOC(=O)CCc1ccc(OC(=O)NCCCCCNC(=O)C(=C)C)cc1]

In some embodiments, the particles can include dimethyl acrylamide, glycerol monomethacrylate, and PPA3 or a derivative thereof, crosslinked with

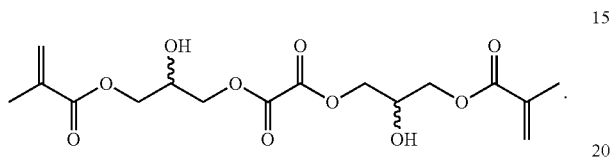

In some embodiments, the particles can include dimethyl acrylamide, glycerol monomethacrylate, and PPA4 or a derivative thereof, crosslinked with

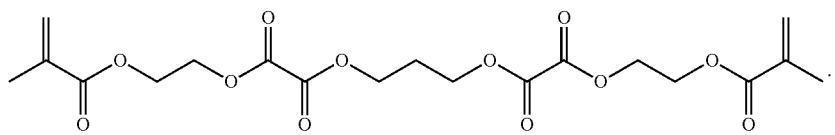 [SMILES: C=C(C)C(=O)OCCOC(=O)C(=O)OCCCOC(=O)C(=O)OCCOC(=O)C(=C)C]

In some embodiments, the particles can include dimethyl acrylamide, glycerol monomethacrylate, and PPA4 or a derivative thereof, crosslinked with

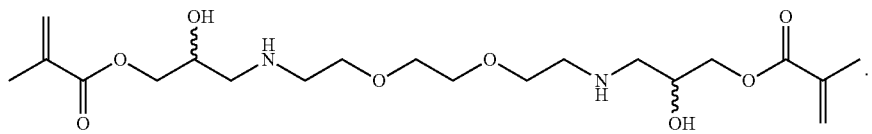 [SMILES: C=C(C)C(=O)OCC(O)CNCCOCCOCCNCC(O)COC(=O)C(=C)C]

In some embodiments, the particles can include dimethyl acrylamide, glycerol monomethacrylate, and PPA4 or a derivative thereof, crosslinked with

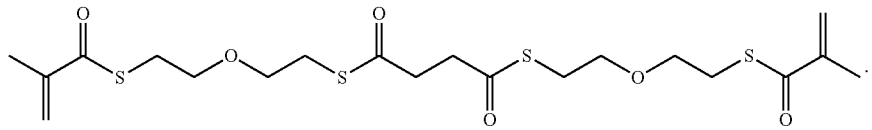 [SMILES: C=C(C)C(=O)SCCOCCSC(=O)CCC(=O)SCCOCCSC(=O)C(=C)C]

In some embodiments, the particles can include dimethyl acrylamide, glycerol monomethacrylate, and PPA4 or a derivative thereof, crosslinked with

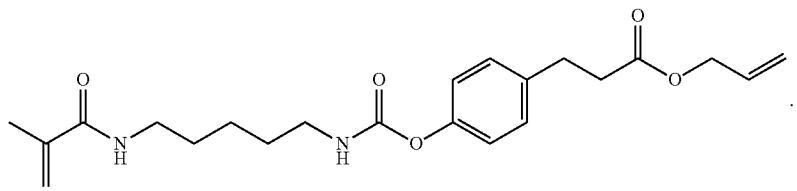 [SMILES: C=CCOC(=O)CCc1ccc(OC(=O)NCCCCCNC(=O)C(=C)C)cc1]

In some embodiments, the particles can include dimethyl acrylamide, glycerol monomethacrylate, and PPA4 or a derivative thereof, crosslinked with

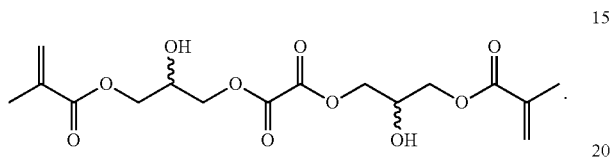

In some embodiments, the particles can include dimethyl acrylamide, glycerol monomethacrylate, and PPA5 or a derivative thereof, crosslinked with

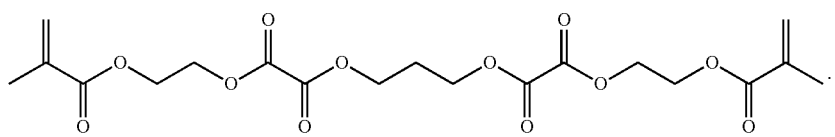 [SMILES: C=C(C)C(=O)OCCOC(=O)C(=O)OCCCOC(=O)C(=O)OCCOC(=O)C(=C)C]

In some embodiments, the particles can include dimethyl acrylamide, glycerol monomethacrylate, and PPA5 or a derivative thereof, crosslinked with

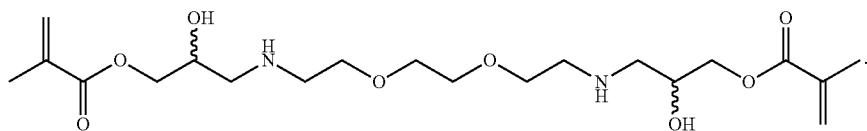 [SMILES: C=C(C)C(=O)OCC(O)CNCCOCCOCCNCC(O)COC(=O)C(=C)C]

In some embodiments, the particles can include dimethyl acrylamide, glycerol monomethacrylate, and PPA5 or a derivative thereof, crosslinked with

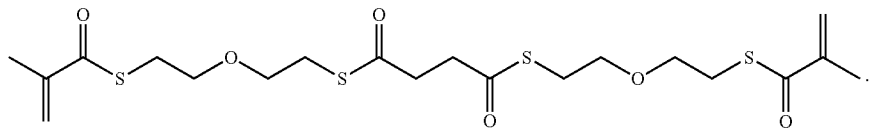 [SMILES: C=C(C)C(=O)SCCOCCSC(=O)CCC(=O)SCCOCCSC(=O)C(=C)C]

In some embodiments, the particles can include dimethyl acrylamide, glycerol monomethacrylate, and PPA5 or a derivative thereof, crosslinked with

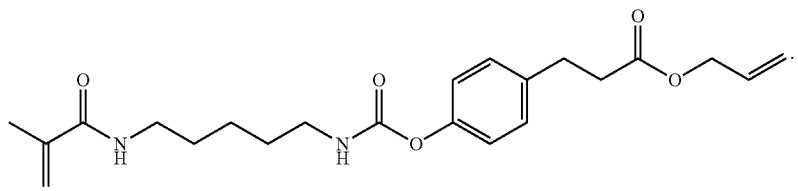 [SMILES: C=CCOC(=O)CCc1ccc(OC(=O)NCCCCCNC(=O)C(=C)C)cc1]

In some embodiments, the particles can include dimethyl acrylamide, glycerol monomethacrylate, and PPA5 or a derivative thereof, crosslinked with

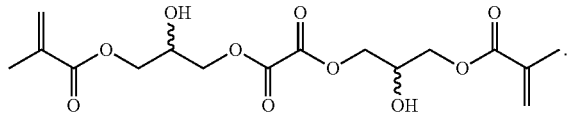 [SMILES: C=C(C)C(=O)OCC(O)COC(=O)C(=O)OCC(O)COC(=O)C(=C)C]

In some embodiments, the particles can include dimethyl acrylamide, glycerol monomethacrylate, and PPA6 or a derivative thereof, crosslinked with

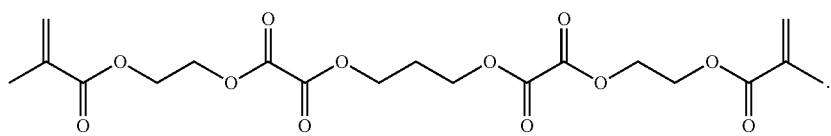 [SMILES: C=C(C)C(=O)OCCOC(=O)C(=O)OCCCOC(=O)C(=O)OCCOC(=O)C(=C)C]

In some embodiments, the particles can include dimethyl acrylamide, glycerol monomethacrylate, and PPA6 or a derivative thereof, crosslinked with

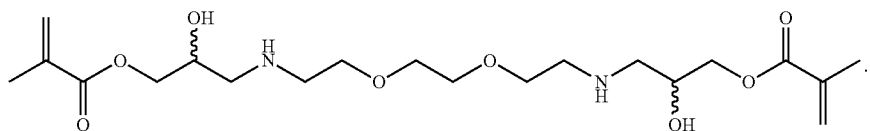 [SMILES: C=C(C)C(=O)OCC(O)CNCCOCCOCCNCC(O)COC(=O)C(=C)C]

In some embodiments, the particles can include dimethyl acrylamide, glycerol monomethacrylate, and PPA6 or a derivative thereof, crosslinked with

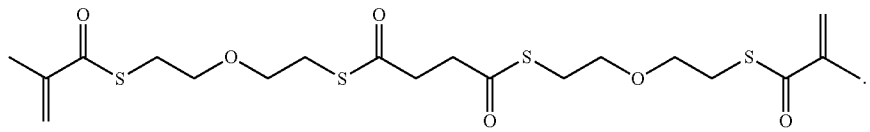 [SMILES: C=C(C)C(=O)SCCOCCSC(=O)CCC(=O)SCCOCCSC(=O)C(=C)C]

In some embodiments, the particles can include dimethyl acrylamide, glycerol monomethacrylate, and PPA6 or a derivative thereof, crosslinked with

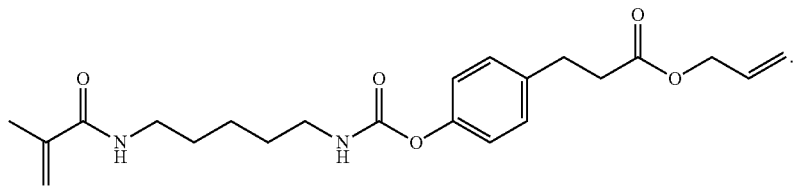 [SMILES: C=CCOC(=O)CCc1ccc(OC(=O)NCCCCCNC(=O)C(=C)C)cc1]

In some embodiments, the particles can include dimethyl acrylamide, glycerol monomethacrylate, and PPA6 or a derivative thereof, crosslinked with

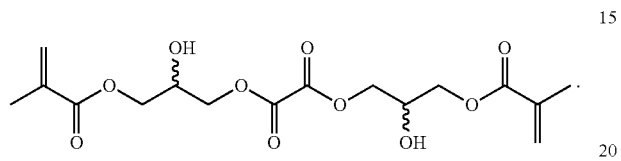

In some embodiments, the particles can include dimethyl acrylamide, glycerol monomethacrylate, and PPA7 or a derivative thereof, crosslinked with

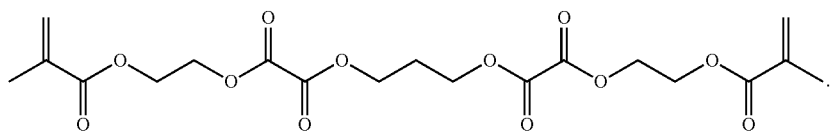 [SMILES: C=C(C)C(=O)OCCOC(=O)C(=O)OCCCOC(=O)C(=O)OCCOC(=O)C(=C)C]

In some embodiments, the particles can include dimethyl acrylamide, glycerol monomethacrylate, and PPA7 or a derivative thereof, crosslinked with

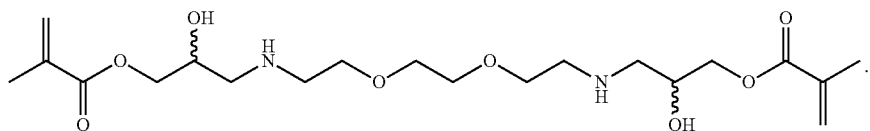 [SMILES: C=C(C)C(=O)OCC(O)CNCCOCCOCCNCC(O)COC(=O)C(=C)C]

In some embodiments, the particles can include dimethyl acrylamide, glycerol monomethacrylate, and PPA7 or a derivative thereof, crosslinked with

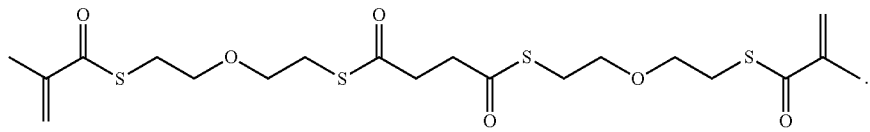 [SMILES: C=C(C)C(=O)SCCOCCSC(=O)CCC(=O)SCCOCCSC(=O)C(=C)C]

In some embodiments, the particles can include dimethyl acrylamide, glycerol monomethacrylate, and PPA7 or a derivative thereof, crosslinked with

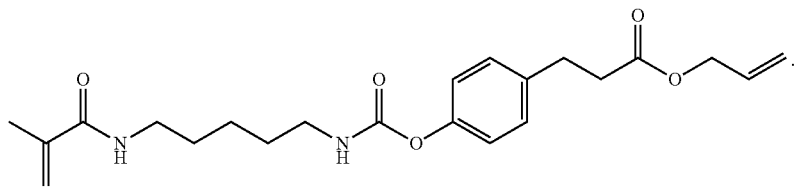 [SMILES: C=CCOC(=O)CCc1ccc(OC(=O)NCCCCCNC(=O)C(=C)C)cc1]

In some embodiments, the particles can include dimethyl acrylamide, glycerol monomethacrylate, and PPA7 or a derivative thereof, crosslinked with

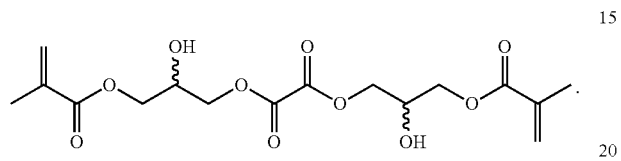

In some embodiments, the particles can include dimethyl acrylamide, glycerol monomethacrylate, and PPA8 or a derivative thereof, crosslinked with

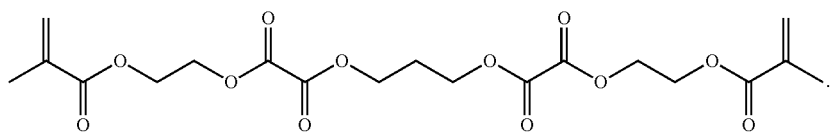 [SMILES: C=C(C)C(=O)OCCOC(=O)C(=O)OCCCOC(=O)C(=O)OCCOC(=O)C(=C)C]

In some embodiments, the particles can include dimethyl acrylamide, glycerol monomethacrylate, and PPA8 or a derivative thereof, crosslinked with

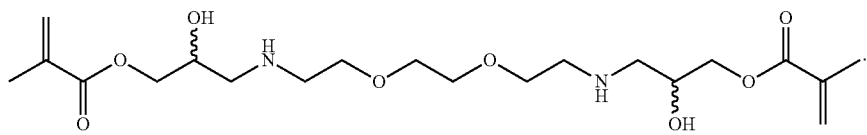 [SMILES: C=C(C)C(=O)OCC(O)CNCCOCCOCCNCC(O)COC(=O)C(=C)C]

In some embodiments, the particles can include dimethyl acrylamide, glycerol monomethacrylate, and PPA8 or a derivative thereof, crosslinked with

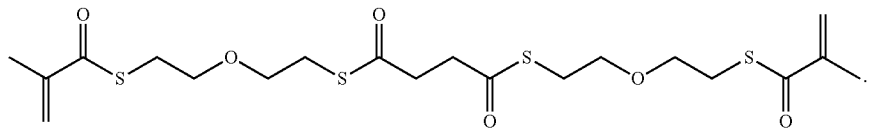 [SMILES: C=C(C)C(=O)SCCOCCSC(=O)CCC(=O)SCCOCCSC(=O)C(=C)C]

In some embodiments, the particles can include dimethyl acrylamide, glycerol monomethacrylate, and PPA8 or a derivative thereof, crosslinked with

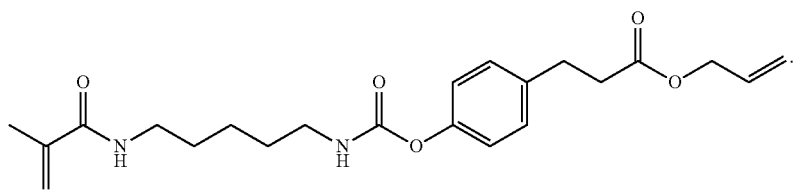 [SMILES: C=CCOC(=O)CCc1ccc(OC(=O)NCCCCCNC(=O)C(=C)C)cc1]

In some embodiments, the particles can include dimethyl acrylamide, glycerol monomethacrylate, and PPA8 or a derivative thereof, crosslinked with

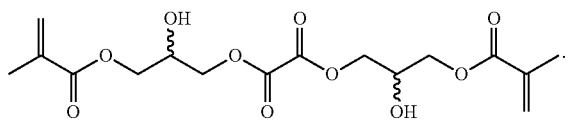 [SMILES: C=C(C)C(=O)OCC(O)COC(=O)C(=O)OCC(O)COC(=O)C(=C)C]

When using the particles to deliver a pharmaceutical agent, the pharmaceutical agent can be delivered over time once delivered. In some embodiments, the pharmaceutical agent/drug can be eluted from the particles at a rate of about 3% to about 5% of the loaded pharmaceutical agent per day. In some embodiments, the total amount of pharmaceutical agent eluted during the first 8 days can be greater than about 30% of the loaded pharmaceutical agent. In some embodiments, the total amount of pharmaceutical agent eluted during the first 8 days can be less than about 40% of the loaded pharmaceutical agent.

In some embodiments, the pharmaceutical agent can have its highest systemic concentration at about 2 hrs, about 3 hrs, about 4 hrs, about 5 hrs, about 6 hrs, about 7 hrs, about 8 hrs, at least about 2 hrs, at least about 3 hrs, or at least about 4 hrs after delivery. In some embodiments, the pharmaceutical agent can be substantially eluted from the polymer particles about 4 days, about 5 days, about 6 days, about 7 days, about 8 days, at least about 2 days, at least about 3 days, at least about 4 days, at most about 8 days, at most about 9 days, or at most about 10 days after delivery.

Example 1

Preparation of a Polymerizable Pharmaceutical Agent

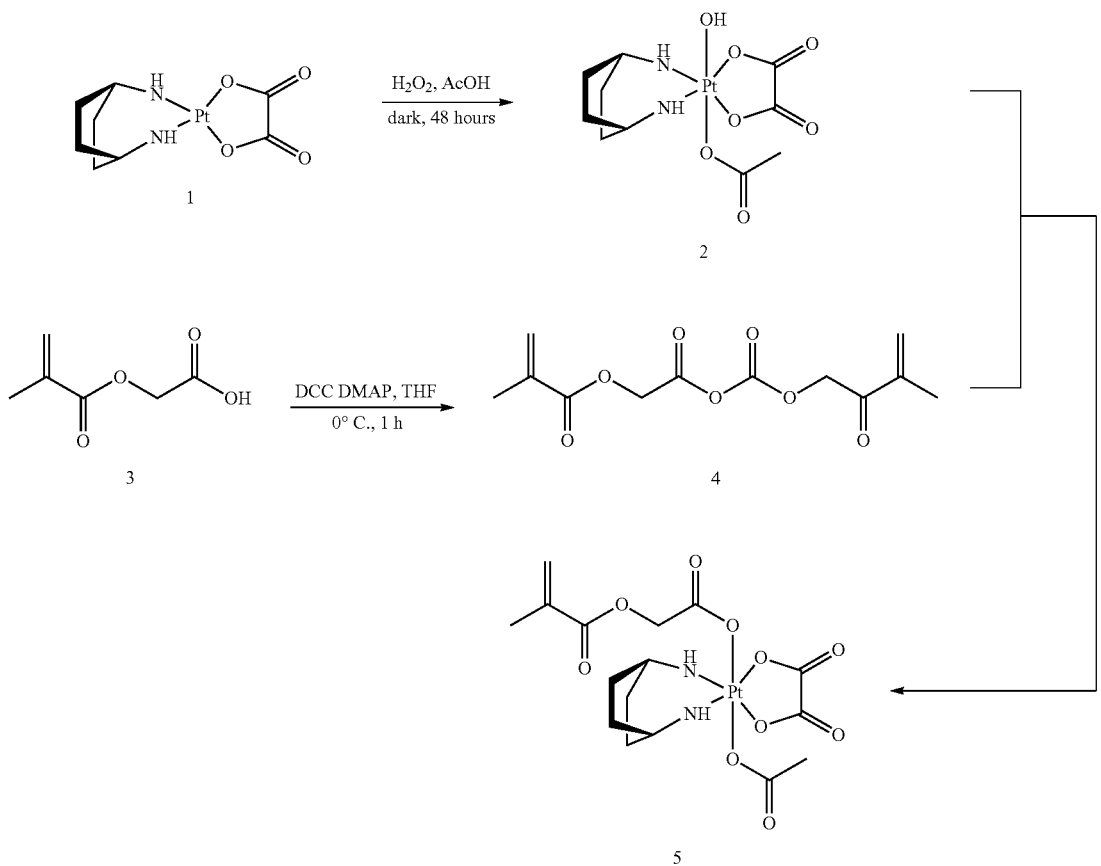

Synthesis of 2: To a 200 mL amber jar fitted with a stir bar was added solid oxaliplatin (1, 8 g, 20.2 mmol). To this solid was added 30% hydrogen peroxide (11.5 mL, 101 mmol) and glacial acetic acid (97 mL, 1.70 mol) sequentially. The bottle was wrapped in aluminum foil and left in the darkness for 48 hours. This step of the synthesis was also run for 24 hours instead of 48. After that the solution was transferred into a 500 mL recovery flask. The solvent was removed by rotary evaporation to leave a residual syrup. Methanol (MeOH) (10 mL) and diethyl ether (Et$_2$O) (100 mL) were added to this residue, which was stirred overnight to induce precipitation. The solid precipitate was collected by filtration and dried under vacuum overnight. The product is a light yellowish solid (8.6909 g). (Zhang, Jenny Z. et al, Chemistry—A European Journal, 2013, 19, 1672-1676.)

Synthesis of 5: To an oven-dried 50 mL Schleck flask fitted with a stir bar was added (methacryloyloxy)acetic acid (3, 1.99 g, 13.78 mmol) and anhydrous tetrahydrofuran (THF) (34.4 mL) under argon. The flask was cooled in an ice bath. To the cooled flask was added dicyclohexylcarbodiimide (DCC) (2.84 g, 13.78 mmol). The solution was stirred for 1 hour while white precipitate began to form. Then a Schleck filtration was performed to remove the precipitate, and the filtrate was collected into a 100 mL oven-dried 3-neck round bottom flask fitted with a stir bar. Mono-acetoxy mono-hydroxy oxaliplatin (2, 5 g, 10.6 mmol) was added to the flask, which was then wrapped in aluminum foil. If necessary, another aliquot of the anhydride can be added to drive the reaction to completion. The reaction was stirred for 17 hours. To work up the reaction, about 160 mL MeOH was added to the reaction. The undissolved solid was separated by filtration. The filtrate was concentrated on a rotary evaporator to a residue, which was later separated on a flash column (silica, MeOH/dichloromethane (DCM)) to yield 5 (0.97 g) as a slightly greenish solid.

Example 2

Preparation of a Polymerizable Pharmaceutical Agent

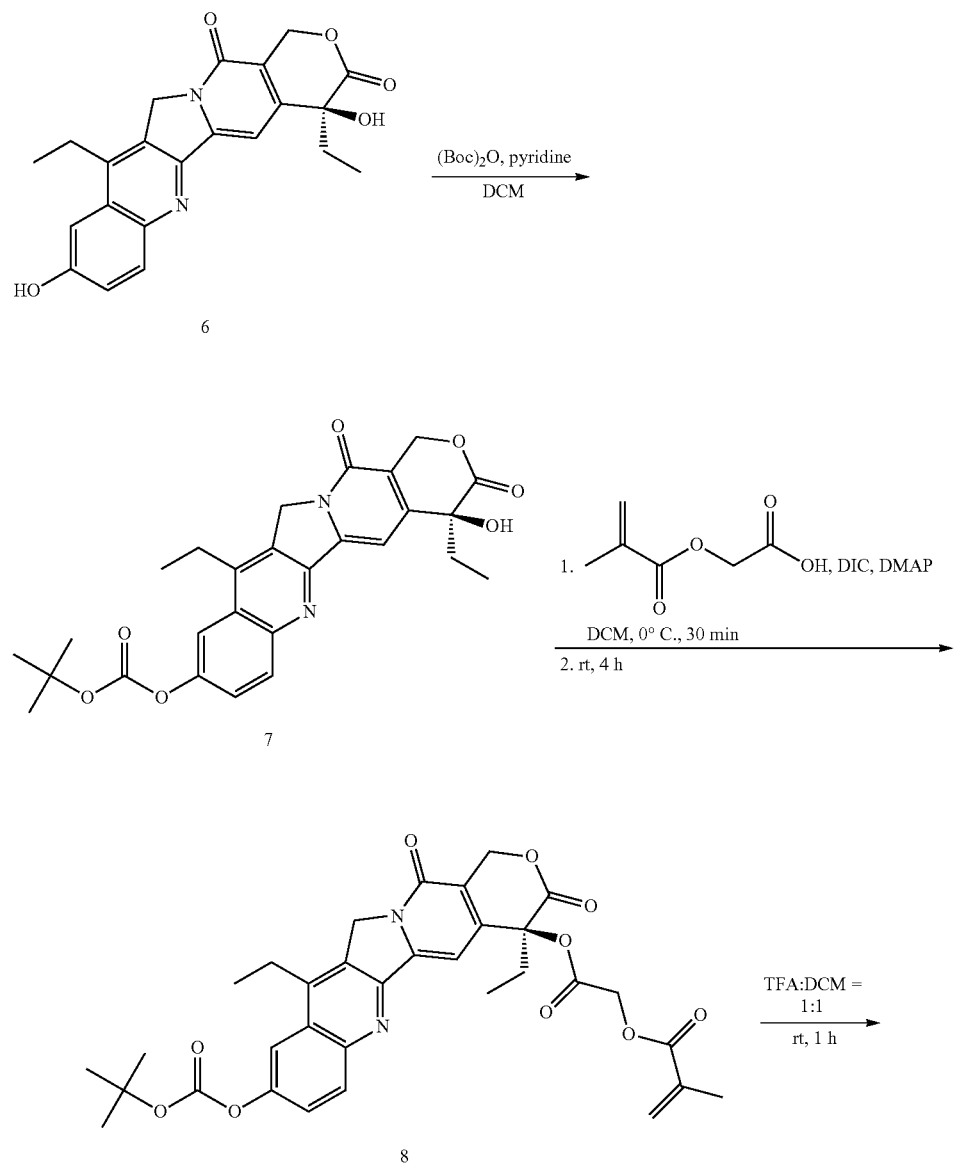

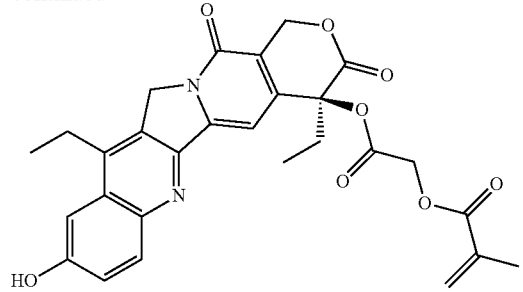

9

Synthesis of 7: To an oven-dried 1000 mL 3-neck round bottom flask fitted with a stir bar was added SN-38 (6, 10 g, 25.5 mmol). Cannula transferred DCM (489 mL) to the flask. Added pyridine (525.3 mmol, 42.3 mL) and di-tert-butyl dicarbonate ($Boc_2O$) (42.3 mL, 33.2 mmol) sequentially to the flask. Stir overnight. To work up, transferred the reaction to a 1 L recovery flask and removed the solvent on a rotary evaporator. Recrystallized the product from boiling isopropanol. Collected the solid by filtration and washed the filtrate with cold isopropanol. Blew dry the solid under argon overnight to yield the product as a light-yellow solid (11.82 g).

Synthesis of 8: To an oven-dried 250 mL 3-neck round bottom flask was added Boc-protected SN-38 (7, 2 g, 4.1 mmol). To this solid was added DCM (82 mL), (methacryloyloxy)acetic acid (3, 590.9 mg, 4.1 mmol), and 4-dimethylaminopyridine (DMAP) (500.9 mg, 4.1 mmol). The flask was cooled in an ice bath before N,N'-diisopropylcarbodiimide (DIC) (642 μL, 4.1 mmol) was added. The reaction was stirred in an ice bath for 30 min. After that, it was stirred under room temperature for 4 hours. To work up the reaction, the reaction mixture was poured over of 0.5% $NaHCO_3$ (10 mL). The organic fraction was collected and washed with 0.1 M HCl (10 mL) before being dried over $Na_2SO_4$. Then the solvent was removed on a rotary evaporator to give the crude product, which was separated on a flash column (silica, acetone/DCM) to give the product as a yellow solid (313.4 mg).

Synthesis of 9: To an oven-dried round bottom flask fitted with a stir bar was added the 8 (1.61 g, 2.6 mmol). To the solid was added anhydrous DCM (26 mL) and trifluoroacetic acid (TFA) (26 mL) sequentially. The solution was stirred at room temperature for 1 hour. Then the solution was transferred to a recovery flask and the solvent was removed on a rotary evaporator. The residue was separated by flash chromatography (silica, DCM/acetone) to yield the product as a light yellow solid (968 mg, 72%).

Example 3

Preparation of a Particle Containing a Polymerizable Pharmaceutical Agent

Mineral oil (300 mL) was added to a sealed jacketed-reaction vessel equipped with an overhead stirring element and a heating element maintained at 85° C. The vessel was sparged with argon for 1-2 hours while mixing. A prepolymer solution was prepared by dissolving 0.96 g acrylamide, 0.64 g hydroxypropyl acrylate, 0.01 g N,N'-methylenebisacrylamide, 0.12 g of azobisisobutyronitrile and 0.40 g of an Oxaliplatin monomer (1), prepared as in Example 1, in 2.0 g of dimethylformamide. Once dissolved, the solution was sparged with argon for 5 min. Azobisisobutyronitrile (0.5 g) was added to the reaction vessel and overhead stirring increased to 400 rpm. After approximately 10 min, an aliquot of SPAN® 80 (1 mL) was added to the mineral oil and allowed to mix. The prepolymer solution was added to the reaction vessel and the resulting suspension was allowed to polymerize for an hour before the heat was turned off. The resulting solution was mixed in the reaction vessel overnight.

Example 4

Preparation of a Particle Containing a Polymerizable Pharmaceutical Agent

Mineral oil (300 mL) was added to a sealed jacketed-reaction vessel equipped with an overhead stirring element and a heating element maintained at 85° C. The vessel was sparged with argon for 1-2 hours while mixing. A prepolymer solution was prepared by dissolving 0.6 g acrylamide, 0.4 g hydroxypropyl acrylate, 0.013 g N,N'-methylenebisacrylamide, 0.075 g of azobisisobutyronitrile and 0.25 g of an SN-38 monomer (2), prepared as in Example 2, in 1.25 g of dimethylformamide. Once dissolved, the solution was sparged with argon for 5 min. Azobisisobutyronitrile (0.5 g) was added to the reaction vessel and overhead stirring increased to 400 rpm. After approximately 10 min, an aliquot of SPAN® 80 (1 mL) was added to the mineral oil and allowed to mix. The prepolymer solution was added to the reaction vessel and the resulting suspension was allowed to polymerize for an hour before the heat was turned off. The resulting solution was mixed in the reaction vessel overnight.

Example 5

Purification of Particles

After the polymerization was complete, the mineral oil was decanted from the reaction vessel and the polymer particles were washed with hexane to remove leftover mineral oil. The particles were separated from the solution and washed with an aliquot of dimethylformamide. Washes with fresh portions of solution were repeated for hexane and dimethylformamide. A final wash was done for 2 hours in dimethylformamide.

The particles were separated by sizes using a sieving process. Sieves were stacked from the largest size (on top) to the smallest size (on bottom). A sieve shaker was utilized to aid in the sieving process. The particles were placed on the top sieve along with an aliquot of dimethylformamide. Once all the particles had been sorted, they were collected and placed in bottles according to their size.

After sieving, the particles were dehydrated to extend their shelf life. Under stirring, the particles were placed in a graded series of acetone/dimethylformamide mixtures. For at least 4 hours, the particles were suspended in solvent mixtures ranging from 75% solvent to 100% solvent. Subsequently, the particles were lyophilized, packaged, and sterilized.

Example 6

In Vitro Elution of Pharmaceutical Agents from Particles

Into a 10 mL plastic syringe, 100 mg of dry SN-38 preloaded particles were added. The particles were suspended in 6 mL of phosphate buffered saline (PBS) and placed at 37° C. oven. At 15 and 30 minutes, 1, 2, 3, 4, 5, and 6 hours, a clean 5 µm filter needle was attached and the extract solution was expelled as much as possible. The particles were re-suspended with another 6 mL of PBS and placed back at 37° C. After the 24 hour sample was collected, the particles were transferred to a 60 mL plastic syringe, suspended in 12 mL of PBS and placed at 37° C. oven. After the 48 hour sample was collected, the particles were suspended in 60 mL of PBS and continued to be suspended in 60 mL of PBS for future time points. The sampling was continued daily for a total of 8 days. The pH of the sample was adjusted to 3 by spiking 1 mL of sample with 10 µL of 0.1 M HCl before chromatographic analysis.

The concentration of SN-38 in each sample was determined using an Agilent 1260 Infinity HPLC system. The chromatographic analysis was performed in a gradient mode with an Agilent Poroshell 120 C18 column (4.6 mm×50 mm, 2.7 µm). The mobile phases delivered at 1 mL/min, consisted of buffer A: acetonitrile and buffer B: 10 mM $KH_2PO_4$, pH 3 and 5% acetonitrile. The chromatographic gradient was 30% buffer A from 0.0-2.0 min, 30-70% from 2.0-2.1 min, 70% from 2.1-4.9 min and 70-30% from 4.9-5.0 min with a post time of 3 mins. The injection volume was 5 µL and the wavelength of the ultraviolet detector was 223 nm. The calibration curve was prepared from 0.5 to 100 ppm of SN-38. The amount of SN-38 released and relative percentage were calculated from the concentration data.

Due to the poor solubility of SN-38 in water and formation of yellow precipitate in the extract solution, volume of extract solution was adjusted from 6 mL to 60 mL for 24 hour samples. The kinetics of SN-38 elution from the preloaded particles is illustrated in FIG. 1. The theoretical amount of SN-38 tethered on the particles is 15 mg for 100 mg of particles assuming no loss of the drug during the preparation of the particles. Upon immersion in PBS, SN-38 was eluted slowly over a period of time. On day 8, there was approximately 3% of SN-38 eluted. The elution curve obtained is fairly close to a linear line over the period of 8 days with a steady daily release between 3-5% of loaded SN-38 indicating controlled release of SN-38 is achieved with the preloaded particles. The total amount of SN-38 eluted during the first 8 days was 34% of the theoretical amount.

Example 7

In Vivo Elution of Pharmaceutical Agents from Particles

Blood samples were obtained to determine the systemic concentration of SN-38 before embolization as well as 20, 40, 60, 120 and 180 minutes post-embolization. An additional blood sample was collected at sacrifice, which was at day 6. Plasma was prepared by centrifugation and the samples were frozen at −80° C. until analysis.

Figure 2:
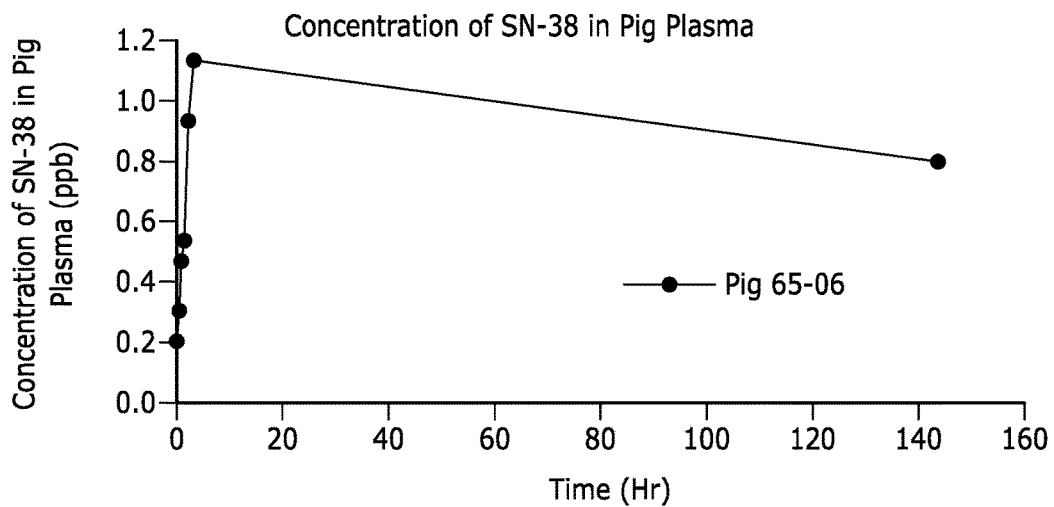
FIG. 2 illustrates the systemic concentration of SN-38 in plasma over time.

Quantitation was done via liquid chromatography-tandem mass spectrometry (LC/MS/MS) using an Agilent 1260 Infinity HPLC system coupled with ABSciex 4000 Q Trap LC/MS/MS system. Chromatographic separation was performed using an Agilent Poroshell 120 C18 column (4.6 mm×50 mm, 2.7 µm) at 25° C. and mobile phases consisting of A: 0.1% formic acid in acetonitrile and B: 0.1% formic acid in water. At a flow rate of 1.0 mL/min, the chromatographic gradient was 27% buffer A from 0.0-0.3 min, 27-52% from 0.3-2.5 min, 52-80% from 2.5-2.6 min, 80% from 2.6-2.7 min, 80-27% from 2.7-2.8 min, 27% from 2.9-4.0 min. The plasma samples were precipitated with 3 fold excess (v/v) of acetonitrile containing 50 ppb of the internal standard, camptothecin. After being vortexed and centrifuged at 13,000 rpm at 4° C. for 10 minutes, 200 µL of the supernatant of each sample was diluted with 600 µL of 0.1% formic acid in water. Injection of 100 µL of the diluted sample was performed. The calibration curve was prepared by spiking blank plasma to a range from 2.5-500 ppb for SN-38. The systemic concentration of SN-38 in plasma over time is illustrated in FIG. 2. At each time point, the concentration of SN-38 was lower than the lower limit of quantitation. The highest systemic concentration was at 3 hrs post embolization and at day 6 the systemic concentration remained similar to 2 hrs post embolization.

Example 8

In Vivo Elution of Pharmaceutical Agents from Particles

Blood samples were obtained to determine the systemic concentration of oxaliplatin before embolization as well as 20, 40, 60, 120 and 180 minutes post-embolization. An additional blood sample was collected at sacrifice, which was at day 6 or day 7. Plasma was prepared by centrifugation and the samples were frozen at −80° C. until analysis.

Figure 3:
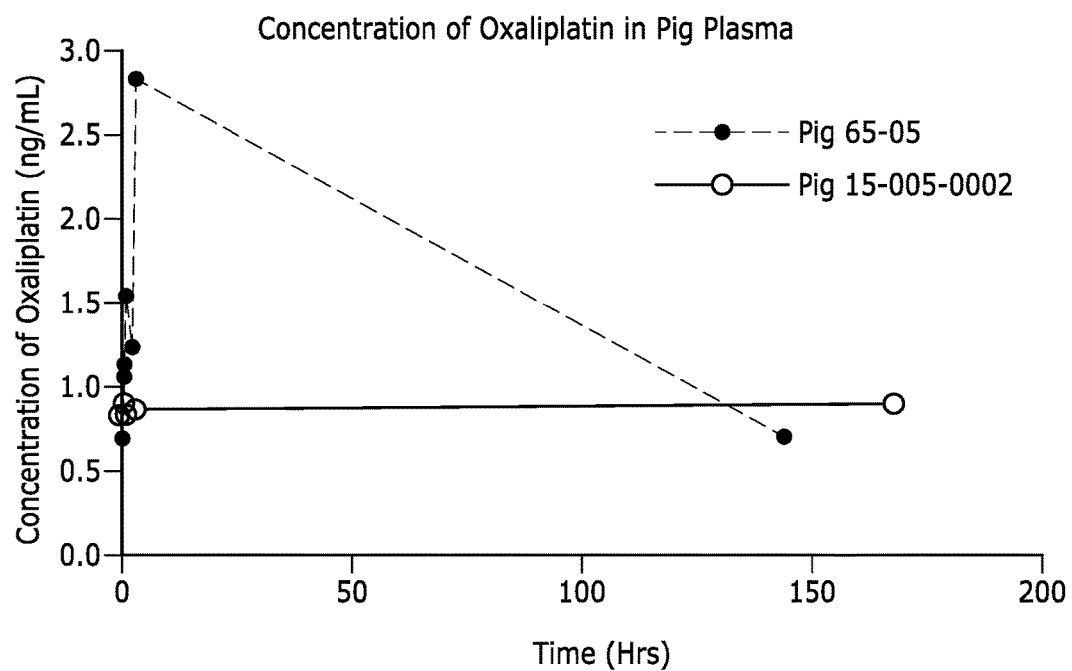
FIG. 3 illustrates the systemic concentration of oxalipatin in plasma over time.

Quantitation was done via LC/MS/MS using an Agilent 1260 Infinity HPLC system coupled with ABSciex 4000 Q Trap LC/MS/MS system. Chromatographic separation was performed using an Agilent Poroshell 120 C18 column (4.6 mm×50 mm, 2.7 µm) at 50° C. and mobile phase consisting of A: 0.1% formic acid in acetonitrile and B: 0.1% formic acid in water. At a flow rate of 500 µL/min, the chromatographic gradient was 0% buffer A from 0.0-2.5 min, 0-90% from 2.5-2.6 min, 90% from 2.6-4.1 min, 90-0% from 4.1-4.2 min, and 0% from 4.2-10.0 min. The divert valve was open from 1.4-2.7 min and 3.4-4.6 min. The plasma samples were purified by ultracentrifugation first and then solid phase extraction. Plasma sample, 500 µL, was loaded onto a 30K Nanosep Centrifuge Device and centrifuged to collect the plasma ultra-filtrate. The centrifugation was performed at 4° C., starting at 8,000 rcf for 30 mins, 9,000 rcf for 30 mins, and 10,000 rcf for 15 mins with an increment of 1,000 rcf every 15 mins until 13,000 rcf for 2 hrs and 15 mins. The collected plasma ultra-filtrate was diluted with 1:1 (v/v) ratio of acetonitrile containing 500 ppb of the internal standard, carboplatin. The mixture, 600 µL, was loaded onto a 1 mL HybridSPE-Phospholipid cartridge, which was placed in a 15 mL conical centrifuge tube and centrifuged at 4° C. at 1,000 rcf for 5 mins and then 4,000 rcf for 5 mins. The sample collected in the centrifuge tube was then transferred to an HPLC vial for analysis. Injection of 50 µL of the sample was performed. The calibration curve was prepared by spiking the blank plasma ultra-filtrate to a range from 5-2000 ppb. The systemic concentration of oxaliplatin in plasma over time is illustrated in FIG. 3. At each time point, the concentration of oxaliplatin was lower than the lower limit of quantitation. For one sample pig, the highest systemic concentration was at 3 hrs post embolization and at day 6 the systemic concentration was close to pre-embolization.

Example 9

Biodegradable Crosslinker

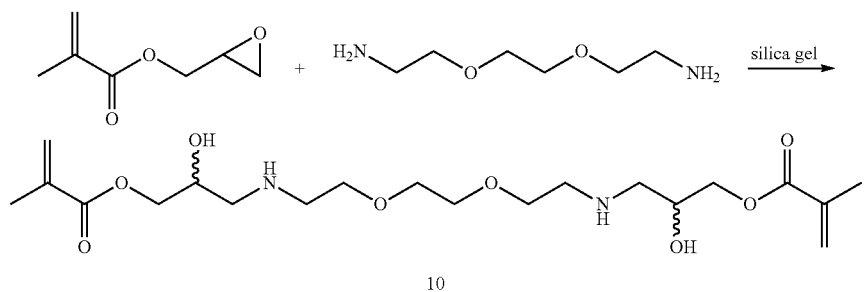

Synthesis of 10: To 2,2'-(ethylenedioxy)bis(ethylamine) (10 g, 67.6 mnol) was added glycidyl methacrylate (10 g, 70.4 mmol) and silica gel (3 g, Aldrich 645524, 60 Å, 200-425 mesh) with good stirring. After stirring for 1 hr, another aliquot of glycidyl methacrylate (9 g, 63.4 mmol) was added and the suspension was stirred for an additional 1.5 hr. The reaction mixture was diluted with chloroform (200 mL) and filtered through a 600 mL fritted glass Buchner funnel of medium porosity, to remove the silica gel. LC-MS analysis of the resultant chloroform solution showed almost no mono-glycidyl amino alcohol and mostly bis-glycidyl amino alcohol, 10 at $(M+H)^+$ 433.2 and was concentrated to about 50 g in vacuo. The resultant heavy syrup was diluted to 100 mL with acetonitrile and stored at $-80°$ C.

Example 10

Biodegradable Crosslinker

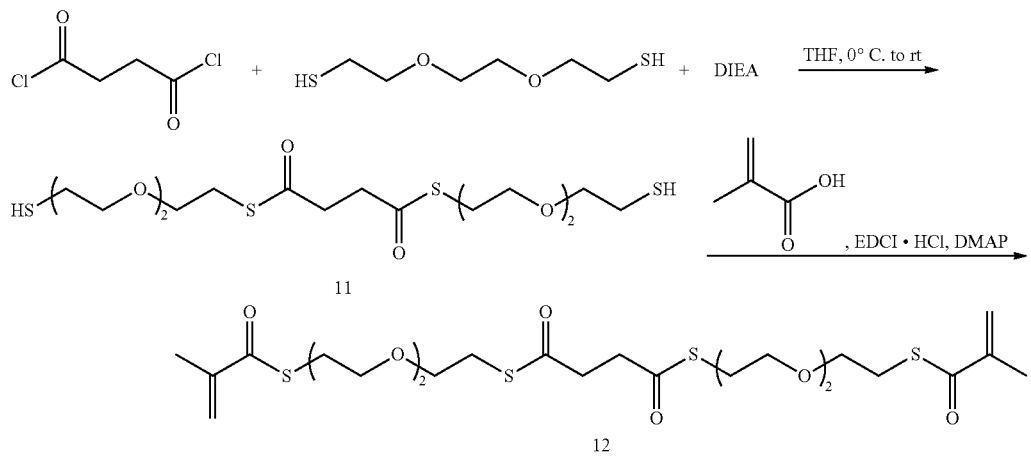

Synthesis of dithioester 11: An oven-dried 250 mL 3-neck round bottom flask was fitted with a stir bar and a 100 mL addition funnel. To this flask was added 3,6-dioxaoctane-1,8-dithiol (20.0 g, 110 mmol), THF (100 mL), and diisopropylamine (DIEA) (15.8 mL, 90.0 mmol) sequentially. The flask was cooled in 0° C. ice bath. Then succinyl chloride (5.0 mL, 45.0 mL) and THF (40 mL) were added to the funnel. The succinyl chloride solution was added dropwise into the reaction mixture, which was stirred overnight. To work up, the brown solution with white precipitate was filtered over a medium-porosity glass fritted funnel. The filtrate was passed through a silica gel plug. The filtrate was concentrated under reduced pressure to give a brown syrup, which was first dissolved in 100 mL DCM. Using gentle swirling, the DCM fraction was washed with 0.1 M NaHCO$_3$ (100 mL) and saturated NaCl solution (100 mL). The DCM fraction was dried over Na$_2$SO$_4$, and the solvent was removed under reduced pressure to give a red liquid (29.65 g). The liquid can be decolorized with activated charcoal, before being separated on a flash column to give 11 as an oily liquid (3.93 g).

Synthesis of tetrathioester 12: A 250 mL 3-neck round bottom flask fitted with a stir bar was dried in the oven. To this round bottom flask was added 11 (2.00 g, 4.48 mmol). DCM (144 mL) was cannula transferred to the flask with stirring. Then methacrylic acid (1.00 g, 11.6 mmol) and DMAP (110 mg, 0.896 mmol) were added to the flask. The reaction flask was cooled in an ice bath first and then added 1-ethyl-3-(3-dimethylaminopropyl)carbodiimide hydrochloride (EDCl.HCl) (2.57 g, 13.4 mmol) portion-wise. The reaction was stirred for 3 hours after the addition. To work up, the reaction was sequentially washed with 1 M NaHCO$_3$ (150 mL) and saturated NaCl (150 mL). The organic fraction was dried over MgSO$_4$ and passed through a silica gel plug. The solvent was removed under reduced pressure to yield the crude product, which was separated on a flash column (normal phase, ethyl acetate/hexanes) to give the product as a clear liquid (1.5 g, 58%).

Example 11

Biodegradable Crosslinker

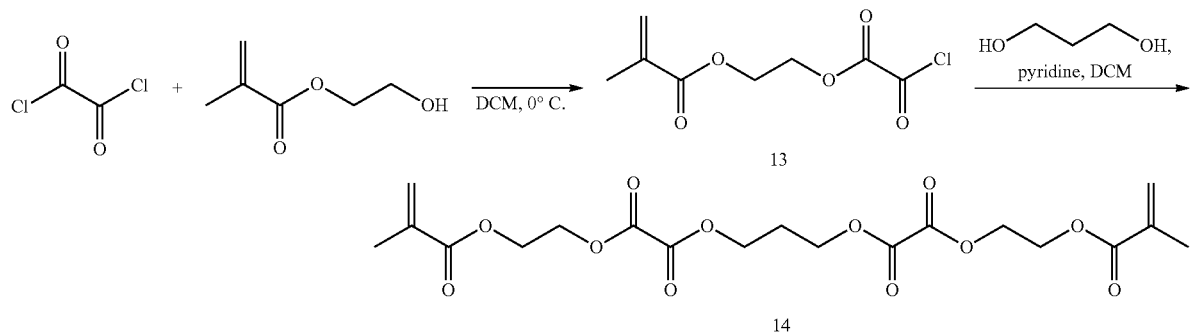

Synthesis of 2-(methacryloxy)ethyl oxalyl monochloride, 13: An oven-dried 100 mL three-neck round bottom flask was purged under argon. The flask was fitted with a stir bar and an addition funnel. To the flask was added oxalyl chloride (20 g, 158 mmol) and anhydrous DCM (15 mL) sequentially. To the addition funnel added 2-hydroxyethyl methacrylate (HEMA) (16 g, 123 mmol). The flask was cooled in an ice bath and added HEMA dropwise to the reaction. After the addition was finished, the flask was left stirring in the ice bath for 1 hour. The flask was pulled out of the ice bath and kept stirring for 1 hour. To work up, removed the DCM and oxalyl chloride on a rotary evaporator. Avoid moisture from here on. The product is a greenish liquid. It does not move on a silica TLC plate and has strong UV absorption. (U.S. Pat. No. 5,395,736 A 19950307)

Synthesis of 14: An oven-dried 50 mL three-neck round bottom flask was purged under argon. Added 2-(methacryloxy)ethyl oxalyl monochloride (13, 12 g, 54.4 mmol) and anhydrous DCM (25.4 mL) to the reaction flask. Added pyridine (5.08 g, 64.2 mmol) and 1,3-propanediol (1.88 g, 24.7 mmol) sequentially to the flask. To work up, began with filtering off the white precipitate. Washed the filtrate with 5% citric acid (50 mL×2). Washed the DCM fraction with saturated sodium chloride (50 mL) and dry over $Na_2SO_4$. The solvent was removed under reduced pressure to give the crude product as a thick yellowish liquid. The product was obtained after a flash column separation (normal phase, ethyl acetate/hexanes) as a clear liquid.

Example 12

Biodegradable Crosslinker

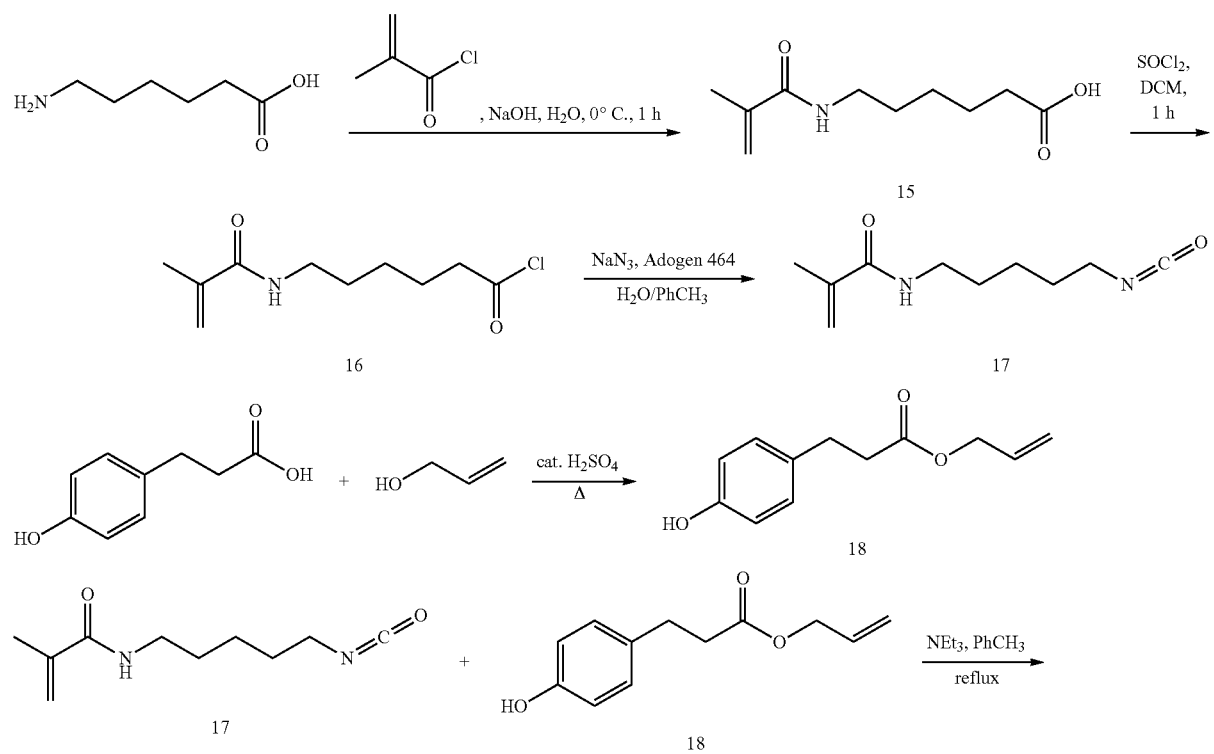

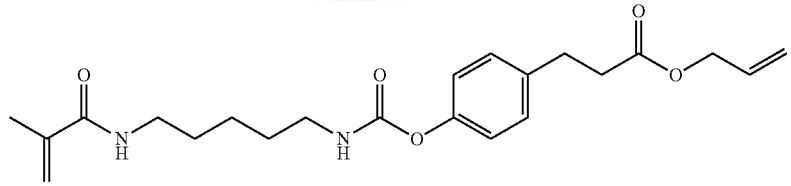

19

Synthesis of 15: In a 50 mL round bottom flask, dissolved 6-aminohexanoic acid (8.45 g, 64.6 mmol) and NaOH (2.6 g, 65 mmol) in ddH₂O (13 mL). The flask was cooled in an ice bath. To this solution was added methacryloyl chloride (6.26 mL, 64 mmol) dropwise and then stirred for two hours. To work up, washed the reaction with DCM (12.5 mL). Kept the aqueous fraction and adjusted the pH of the aqueous layer to 2.0 with 1 M HCl. Extracted the aqueous layer with ethyl acetate (30 mL×3). Combined the organic fraction and dried over Na₂SO₄. Removed the solvent under reduced pressure. The crude product was crystallized with ethyl acetate and hexanes to give the product as clear crystals (4.65 g, 36.5%).

Synthesis of 16: A three-neck round bottom flask was purged under argon. Added 6-(methacryloylamino)hexanoic acid (2.5 g, 12.6 mmol) and DCM (50 mL) to the flask. Added thionyl chloride (4.50 g, 37.8 mmol) dropwise to the solution with stirring. Stirred for one hour. Removed the solvent, thionyl chloride, and the byproduct under reduced pressure to yield the product as a yellowish liquid.

Synthesis of 17: A 100 mL round bottom flask fitted with a stir bar was purged under argon. To this flask was added sodium azide (0.774 g, 11.91 mmol), Adogen 464 (0.011 mL), and ddH₂O (25.1 mL) sequentially. The flask was cooled in ice bath. To this aqueous solution was added toluene (25.1 mL) and 6-[(2-methyl-1-oxo-2-propen-1-yl)amino]hexanoyl chloride (16, 2.47 g, 11.3 mmol) sequentially. Stirred for 45 minutes and removed the aqueous layer thereafter. Wash the organic fraction with ddH₂O (10 mL). Then dried the organic fraction over Na₂SO₄ and decolorized with charcoal. Removed the Na₂SO₄ and charcoal with filtration. Removed the solvent under reduced pressure to yield the product as a clear liquid (0.73 g).

Synthesis of Allyl Ester 18: To a 500 mL three-neck round bottom flask fitted with a stir bar was added 4-hydroxybenzenepropionic acid (50 g, 0.3 mol) and allyl alcohol (204 mL, 3 mol). To this mixture was added sulfuric acid (0.6 g, 6 mmol). The reaction was stirred at 95° C. overnight. The reaction was cooled to room temperature and poured over ddH₂O (200 mL). The aqueous phase was extracted with dichloromethane (150 mL). The organic fraction was subsequently washed with ddH₂O (200 mL), NaHCO₃ solution (200 mL, followed by 150 mL), and brine (200 mL). The organic fraction was dried over MgSO₄ and the solvent was removed on a rotary evaporator. The crude product was decolorized with charcoal and stabilized with phenothiazine (28 mg). The crude product was further purified with flash chromatography (normal phase, hexanes/ethyl acetate) to yield the product as an oily liquid (43.8 g, 70.8%).

Synthesis of Carbamate Crosslinker 19: To an oven-dried three-neck round bottom flask fitted with a stir bar was added phenothiazine (0.7 mg), N-(5-isocyanatopentyl)-2-methyl-2-propenamide (17, 730 mg, 4.31 mmol), toluene (5 mL), and trimethylamine (600 µL) to the flask. A solution of 18 (740 mg, 3.59 mmol) in toluene (6 mL) was added. The solution was placed in an oil bath and refluxed overnight. The solvent was removed at the end of the reaction to obtain the crude product, which was separated on a flash column to yield the product as a white solid (470 mg).

Example 13

Biodegradable Crosslinker

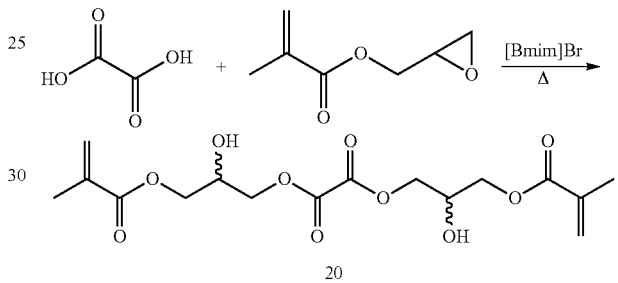

20

Synthesis of Oxalate Diester 20: To a 100 mL round bottom flask with a stir bar was added oxalic acid (5.4 g, 60 mmol), 1-butyl-3-methylimidazolium bromide ([Bmim]Br) (18 g, 84 mmol) and 4-methoxyphenol (120 mg, 0.97 mmol). The content was melted at 90° C. with stirring for 15 minutes. After adding glycidyl methacrylate (17.04 g, 120 mmol), the reaction was stirred at 90° C. for 1 hour. Thin layer chromatography stain with 4-(4-nitrobenzyl)pyridine showed full consumption of the epoxide. The reaction mixture was suspended in 200 mL of ethyl acetate (EtOAc) and washed with water (100 mL×2), saturated sodium bicarbonate (100 mL×2), and brine (100 mL). The organic phase was collected and dried over sodium sulfate. The crude was dried under vacuum and purified with flash chromatography (DCM/EtOAc). Total of 12.7 g of purified product was obtained as a clear liquid.

Example 14

Preparation of a Polymerizable Pharmaceutical Agent

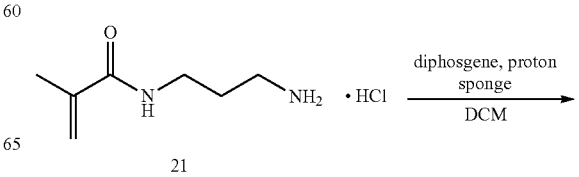

21

-continued

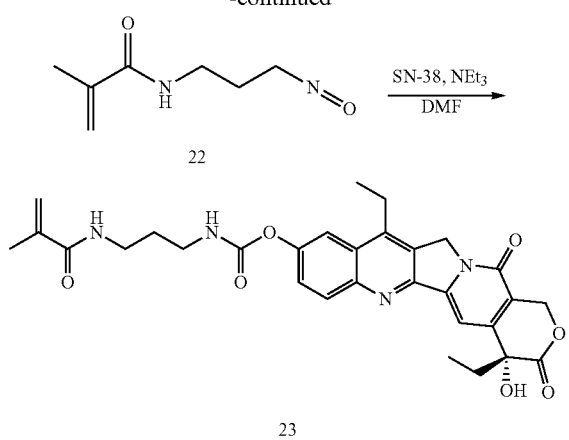

Synthesis of 22: 3-aminopropyl methacrylamide hydrochloride (21) is suspended in a solution of proton sponge in anhydrous dichloromethane. This suspension is added dropwise to an ice-cold solution of diphosgene in anhydrous dichloromethane. After the reaction is over, the solvent is removed under reduced pressure. The residue is re-dissolved in dichloromethane and washed successively with 1N HCl and 1N NaOH. The organic fraction is stabilized with phenothiazine and dried over $MgSO_4$. The solvent is removed under reduced pressure to afford 22.

Synthesis of 23: To a suspension of SN-38 in anhydrous DMF was added 22, followed by triethylamine. The reaction can be driven to completion by optional heating. Upon completion, the solvent is removed under reduced pressure. The residue can be purified by crystallization or flash chromatography.

Example 15

Preparation of Polymerizable Pharmaceutical Agent

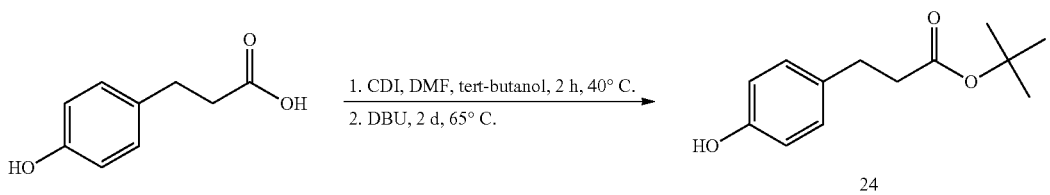

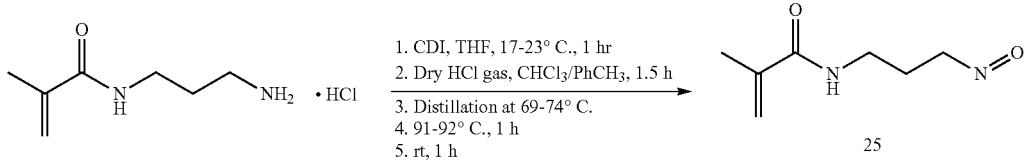

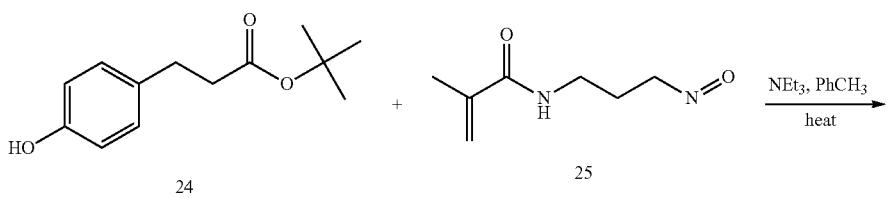

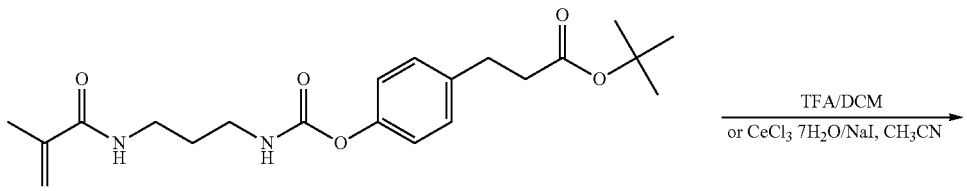

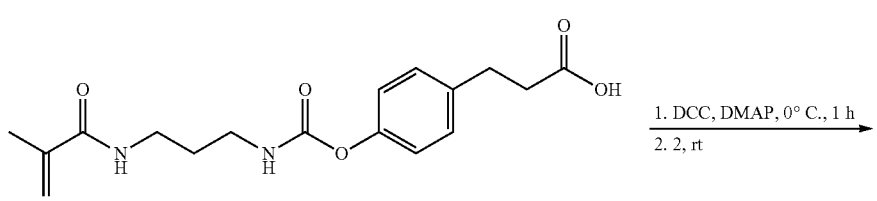

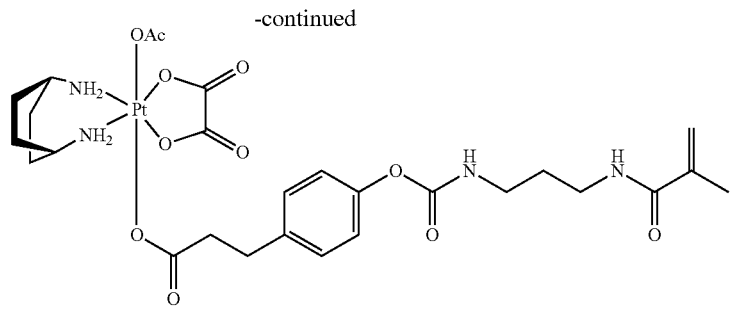

28

Synthesis of 3-(4-Hydroxyphenyl)-propionic acid t-butyl ester (24): To a solution of 3-(4-Hydroxyphenyl)-propionic acid in dimethylformamide was carefully added carbonyl diimidazole. The reaction mixture was stirred at 40° C. for 2 hours. DBU and t-butanol were then added and the reaction mixture was stirred at 65° C. for 2 days after which time TLC indicated that the starting material had been consumed. The reaction mixture was cooled to room temperature, water (40 mL) added and the product extracted with MTBE. The organic fraction was dried, concentrated under reduced pressure and the product isolated by flash column chromatography to give the product as a colorless oil.

Synthesis of 2-methyl-acrylic acid 3-isocyanato-propyl amide (25): CDI is suspended in dry THF at room temperature. The suspension is cooled to 17° C. After about 30 min stirring, APMA hydrochloride is added to the mixture under cooling on ice portion-wise during while keeping the reaction temperature at 23° C. A yellow suspension was obtained. After about 3 hours of stirring, the suspension is filtered. The filtration was stabilized with phenothiazine and concentrated to obtain 2-methyl-acrylic acid 3-[(imidazole-1-carbonyl-amino]-propyl amide as a clear orange resin. 2-methyl-acrylic acid 3-[(imidazole-1-carbonyl-amino]-propyl amide is dissolved in anhydrous chloroform at room temperature. The solution is then diluted with toluene. To this suspension is added dry hydrochloride gas within about 30 min, while cooling. After a clear liquid phase is formed, stir this reaction for another hour. Then distilled chloroform from this reaction mixture while heating it to 69-74° C. Then the reaction will be kept at 91-92° C. for 1 hour. Then stir for 1 hour at room temperature. The toluene phase is collected and concentrated in darkness. Distill the residue at 48° C. to obtain the final product as a colorless oil. (To generate dry hydrogen chloride gas, slowly drip concentrated hydrogen chloride solution from an addition funnel into anhydrous calcium chloride. The gas evolved can be directed bubbled into the reaction.)

To synthesize 26, react 24 and 25 in the presence of triethyl amine using toluene as a solvent. The reaction can be refluxed overnight if necessary.

De-protection of 26: 26 is stirred in a 50/50 v/v mixture of TFA and DCM at room temperature for one hour. The solvent and TFA is then removed on a rotovap. The residue will be purified on a flash chromatography. Alternatively, it can be de-protected in a mixture of $CeCl_3.7H_2O/NaI$ in acetonitrile. Work up include dilution with ether and acidification with HCl. The HCl phase will then be extracted with diethyl ether. The ether phases are combined and dried over $Na_2SO_4$. The concentrated ether phase is purified by flash chromatography to afford 27.

Synthesis of 28: 27 can be prepared via the anhydride method or direct coupling method. To perform the direct coupling method, 27 is dissolved in anhydrous THF under inert atmosphere. To this solution is added DMAP and the oxaliplatin complex 2. The flask is cooled in ice bath. Then DCC will be added portion-wise. The reaction is allowed to stir overnight before being filtered to obtain the filtrate. The filtrate is concentrated and separated on a normal phase column to obtain 28. The anhydride method is similar to what was described in Example 1.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents and printed publications throughout this specification. Each of the above-cited references and printed publications are individually incorporated herein by reference in their entirety.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

We claim:

1. A particle including:
   at least one monomer amenable to polymerization;
   at least one crosslinker; and
   at least one polymerizable pharmaceutical agent chemically bonded to the particle with a hydrolytically degradable linkage.

2. The particle of claim 1, wherein the particle is biostable.

3. The particle of claim 1, wherein the crosslinker is biostable.

4. The particle of claim 1, wherein the particle is biodegradable.

5. The particle of claim 1, wherein the at least one monomer amenable to polymerization includes glycerol monomethacrylate.

6. The particle of claim 1, wherein the at least one monomer amenable to polymerization includes dimethyl acrylamide.

7. The particle of claim 1, wherein the crosslinker is biodegradable.

8. The particle of claim 1, wherein the polymerizable pharmaceutical agent has a structure

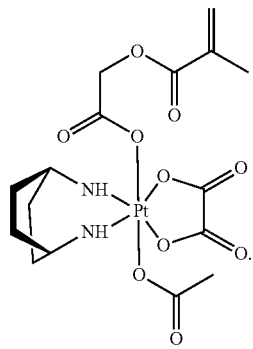

9. The particle of claim 1, wherein the polymerizable pharmaceutical agent has a structure

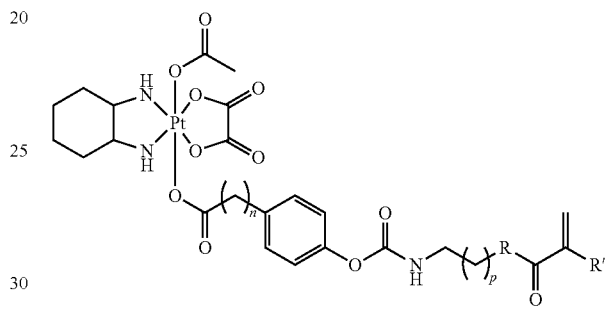

wherein n is 0, 1, 2, 3, 4, 5, 6, 7, 8, 9, 10, 11, or 12;
p is 1, 2, 3, 4, 5, 6, 7, 8, 9, 10, 11, or 12;
R is N or NH; and
R' is H or $CH_3$.

10. The particle of claim 1, wherein the polymerizable pharmaceutical agent has a structure

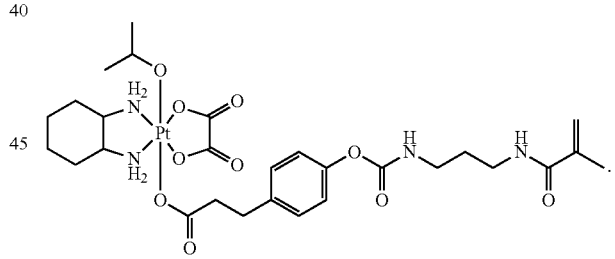

11. The particle of claim 1, wherein the polymerizable pharmaceutical agent has a structure

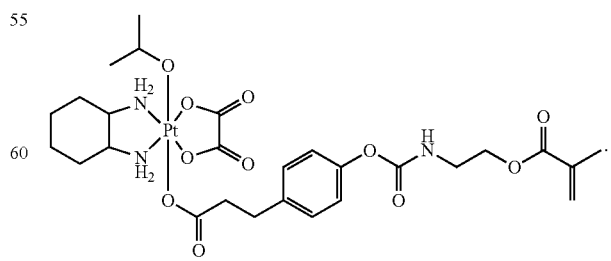

12. The particle of claim 1, wherein the polymerizable pharmaceutical agent has a structure

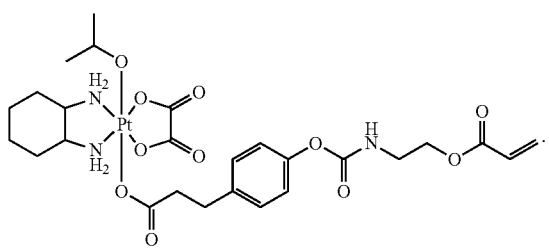

13. The particle of claim 1, wherein the polymerizable pharmaceutical agent has a structure

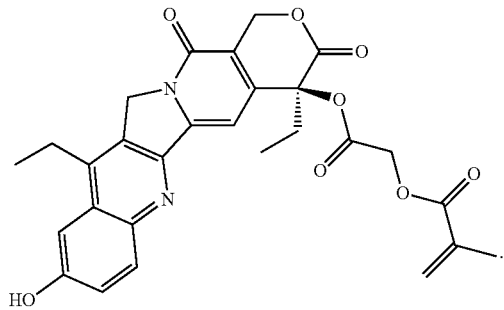 [SMILES: C=C(C)C(=O)OCC(=O)O[C@]1(CC)C(=O)OCc2c1cc1n(c2=O)Cc2c-1nc1ccc(O)cc1c2CC]

14. The particle of claim 1, wherein the polymerizable pharmaceutical agent has a structure

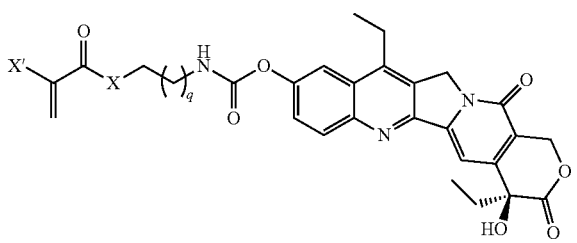

wherein q is 1, 2, 3, 4, 5, 6, 7, 8, 9, 10, 11, or 12;
X is O or NH; and
X' is H or $CH_3$.

15. The particle of claim 1, wherein the polymerizable pharmaceutical agent has a structure

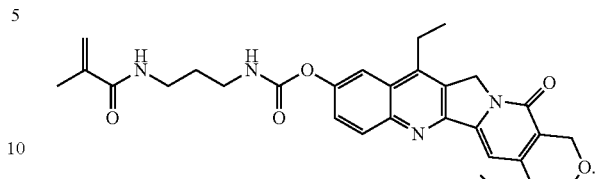

16. The particle of claim 1, wherein the polymerizable pharmaceutical agent has a structure

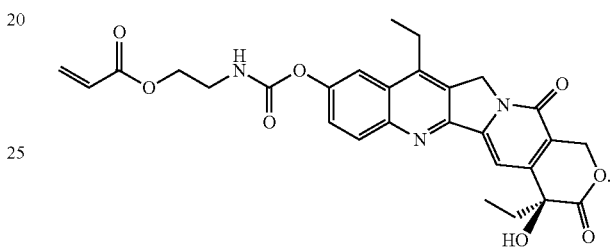

17. The particle of claim 1, wherein the polymerizable pharmaceutical agent has a structure

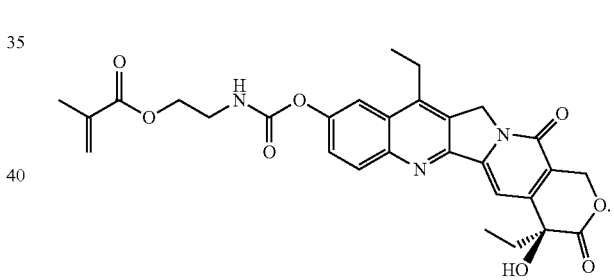

18. The particle of claim 1, wherein the crosslinker is

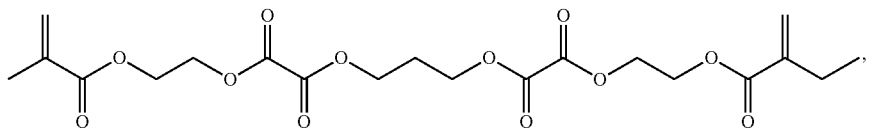

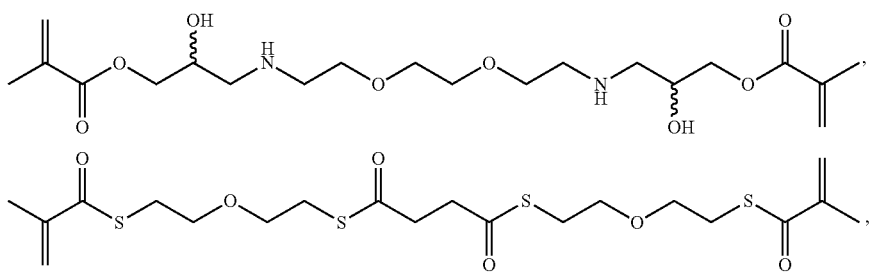

-continued
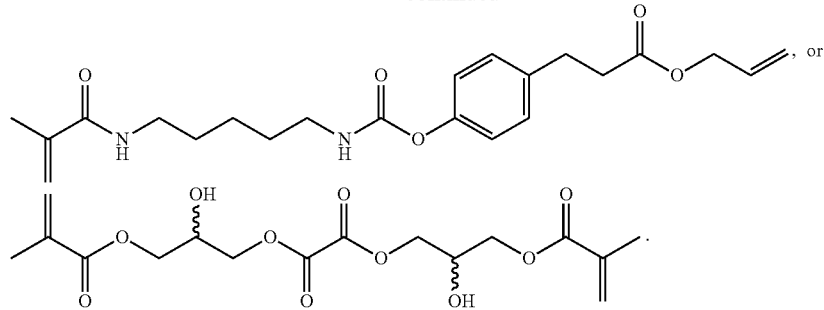

UNITED STATES PATENT AND TRADEMARK OFFICE
CERTIFICATE OF CORRECTION

PATENT NO. : 10,328,175 B2  
APPLICATION NO. : 15/719197  
DATED : June 25, 2019  
INVENTOR(S) : Gregory M. Cruise et al.

Page 1 of 3

It is certified that error appears in the above-identified patent and that said Letters Patent is hereby corrected as shown below:

In the Claims

In Claim 10 (Column 50, Line 45), please replace

" 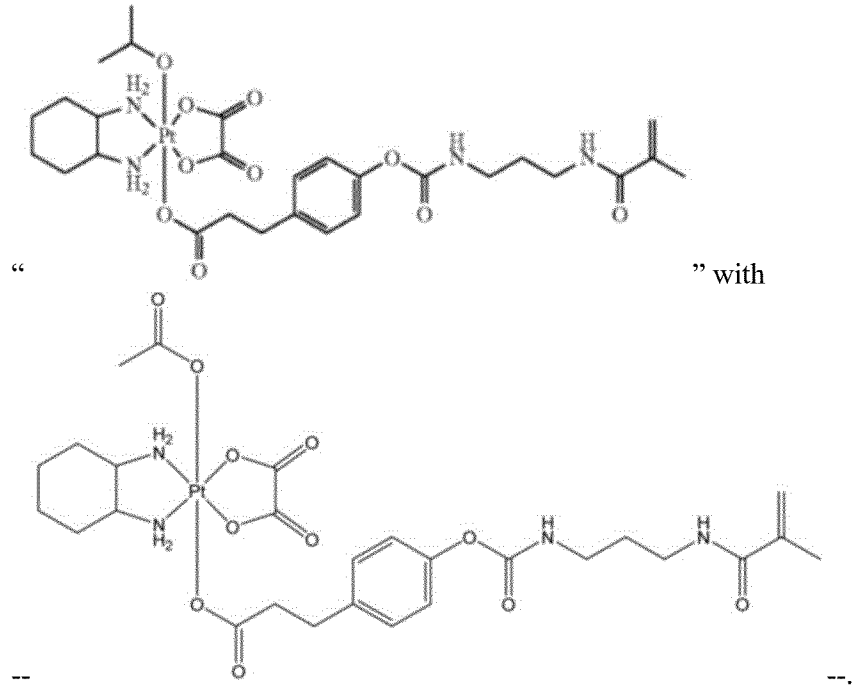 " with

"  " --.

Signed and Sealed this  
Twenty-fourth Day of December, 2019

Andrei Iancu  
*Director of the United States Patent and Trademark Office*

CERTIFICATE OF CORRECTION (continued)
U.S. Pat. No. 10,328,175 B2

In Claim 11 (Column 50, Line 60), please replace

" 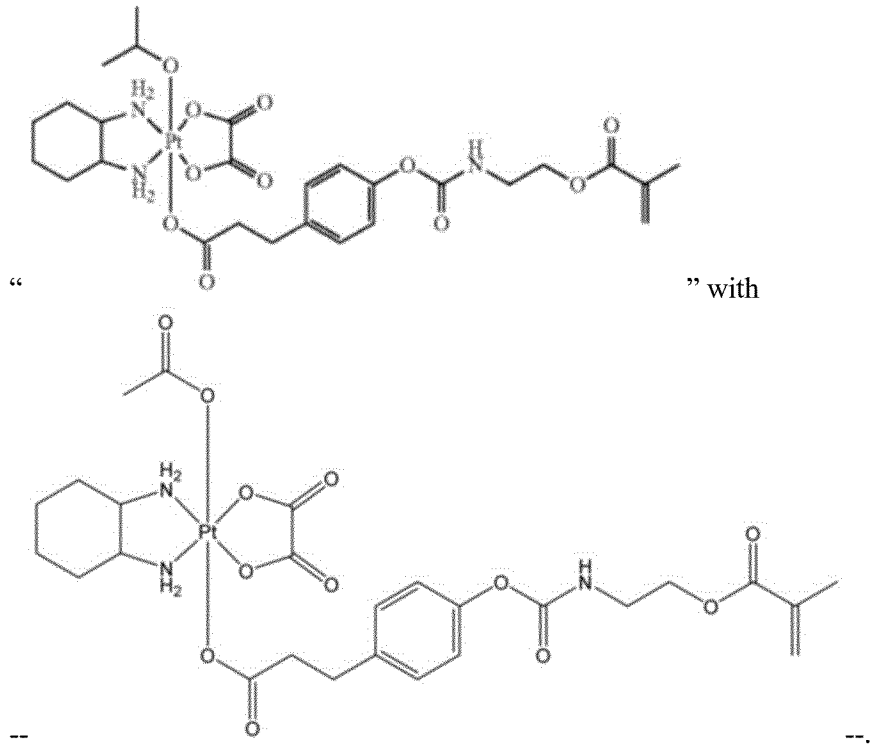 " with

-- --.

In Claim 12 (Column 51, Line 5), please replace

" 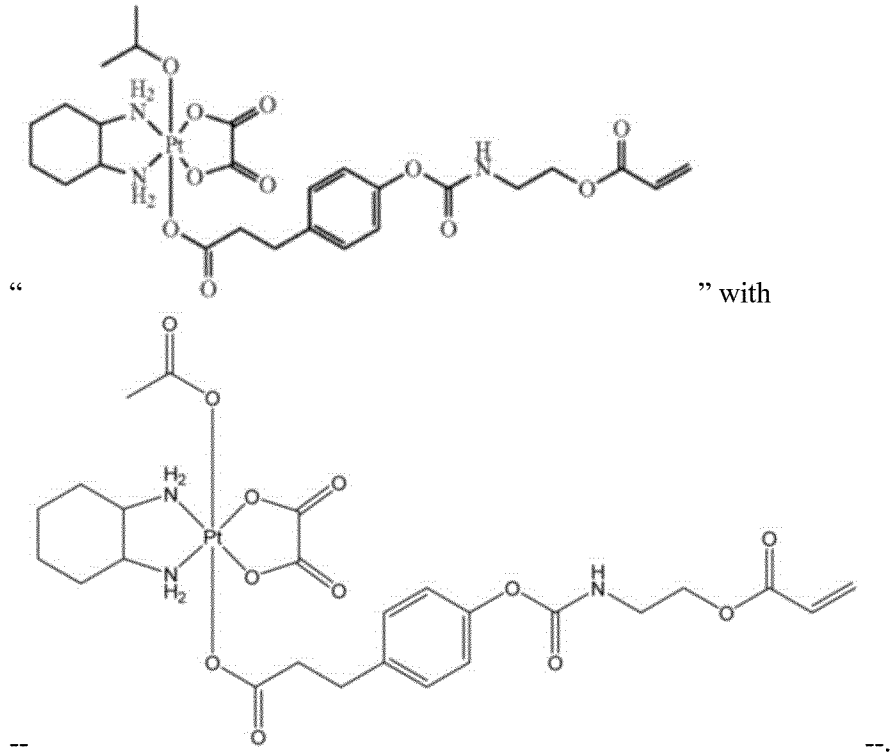 " with

-- --.

In Claim 18 (Column 52, Line 50), please replace "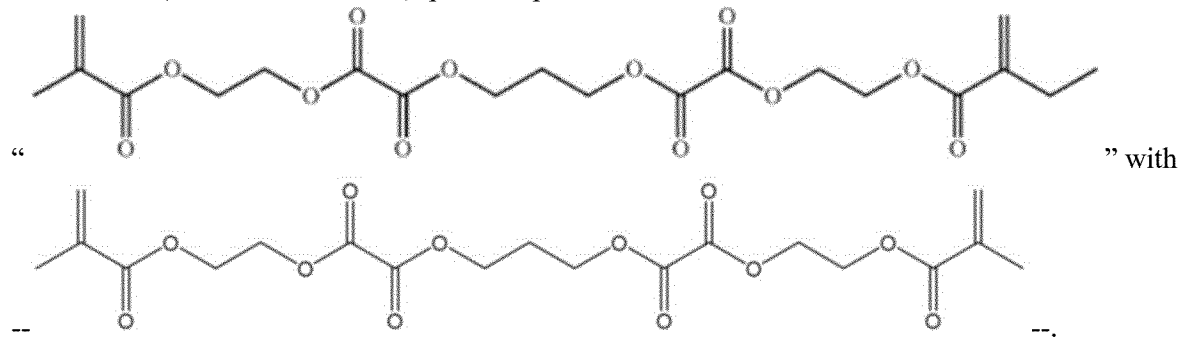" with --
--.